US011621057B2

(12) United States Patent
Steingrimsson et al.

(10) Patent No.: US 11,621,057 B2
(45) Date of Patent: Apr. 4, 2023

(54) CLASSIFIER GENERATION METHODS AND PREDICTIVE TEST FOR OVARIAN CANCER PATIENT PROGNOSIS UNDER PLATINUM CHEMOTHERAPY

(71) Applicant: Biodesix, Inc., Boulder, CO (US)

(72) Inventors: Arni Steingrimsson, Steamboat Springs, CO (US); Joanna Röder, Steamboat Springs, CO (US); Julia Grigorieva, Steamboat Springs, CO (US); Heinrich Röder, Steamboat Springs, CO (US); Krista Meyer, Steamboat Springs, CO (US)

(73) Assignee: BIODESIX, INC., Boulder, CO (US)

( * ) Notice: Subject to any disclaimer, the term of this patent is extended or adjusted under 35 U.S.C. 154(b) by 1213 days.

(21) Appl. No.: 16/092,023

(22) PCT Filed: Mar. 10, 2017

(86) PCT No.: PCT/US2017/021736
§ 371 (c)(1),
(2) Date: Oct. 8, 2018

(87) PCT Pub. No.: WO2017/176423
PCT Pub. Date: Oct. 12, 2017

(65) Prior Publication Data
US 2022/0108771 A1    Apr. 7, 2022

Related U.S. Application Data

(60) Provisional application No. 62/319,958, filed on Apr. 8, 2016.

(51) Int. Cl.
*G16B 40/00*    (2019.01)
*G16B 40/20*    (2019.01)
*G16H 20/40*    (2018.01)

(52) U.S. Cl.
CPC .......... *G16B 40/00* (2019.02); *G16B 40/20* (2019.02); *G16H 20/40* (2018.01)

(58) Field of Classification Search
CPC ..... G16H 50/20; H01J 49/0027; G16B 40/20; A61P 35/00
(Continued)

(56) References Cited

U.S. PATENT DOCUMENTS

| 7,736,905 B2 | 6/2010 | Roder |
| 7,858,389 B2 | 12/2010 | Roder |
| 7,858,390 B2 | 12/2010 | Roder |
| 7,867,775 B2 | 1/2011 | Roder |
| 7,879,620 B2 | 2/2011 | Roder |
| 7,906,342 B2 | 3/2011 | Roder |

(Continued)

OTHER PUBLICATIONS

Google patents search, Feb. 24, 2022 (Year: 2022).*
ip.com search, Feb. 25, 2022 (Year: 2022).*
(Continued)

*Primary Examiner* — Dilek B Cobanoglu
(74) *Attorney, Agent, or Firm* — DLA Piper LLP US

(57) ABSTRACT

A method of generating a classifier includes a step of classifying each member of a development set of samples with a class label in a binary classification scheme with a first classifier; and generating a second classifier using a classifier development process with an input classifier development set being the members of the development set assigned one of the two class labels in the binary classification scheme by the first classifier. The second classifier stratifies the members of the set with an early label into two further sub-groups. We also describe identifying a plurality of different clinical sub-groups within the development set based on the clinical data and for each of the different clinical sub-groups, conducting a classifier generation process for each of the clinical sub-groups thereby generating clinical subgroup classifiers. We further describe an example
(Continued)

of a hierarchical arrangement of such classifiers and their use in predicting, in advance of treatment, ovarian cancer patient outcomes on platinum-based chemotherapy.

11 Claims, 18 Drawing Sheets

(58) Field of Classification Search
USPC .............................................. 703/11; 702/19
See application file for complete search history.

(56) References Cited

U.S. PATENT DOCUMENTS

| | | | |
|---|---|---|---|
| 8,024,282 B2 | 9/2011 | Tsypin | |
| 8,718,996 B2* | 5/2014 | Roder | ..................... G16H 50/20 |
| | | | 703/11 |
| 9,279,798 B2 | 3/2016 | Roder | |
| 9,477,906 B2 | 10/2016 | Roder | |
| 10,007,766 B2 | 6/2018 | Roder | |
| 10,092,567 B2* | 10/2018 | Lin | .......................... A61P 35/00 |
| 2008/0319932 A1 | 12/2008 | Yih | |
| 2009/0105167 A1* | 4/2009 | Potti | ...................... G16B 40/20 |
| | | | 506/17 |
| 2013/0320203 A1 | 12/2013 | Roder | |
| 2014/0200825 A1* | 7/2014 | Roder | ................. H01J 49/0027 |
| | | | 702/19 |
| 2015/0102216 A1 | 4/2015 | Roder | |
| 2016/0321561 A1 | 11/2016 | Roder | |

OTHER PUBLICATIONS

Identification of Cancer Diagnosis Estimation Models Using Evolutionary Algorithms—A Case Study for Breast Cancer, Melanoma, and Cancer in the Respiratory System, Upper Austria University of Applied Sciences Department of Bioinformatics, GECCO'11, Jul. 12-16, 2011, Dublin, Ireland (Year: 2011).*

Colombo et al., "Newly diagnosed and relapsed epithelial ovarian carcinoma: ESMO Clinical Practice Guidelines for diagnosis, treatment and follow-up", Annals of Oncology 21(5) (2010).

Girosi et al., "Regularization Theory and Neural Networks Architectures", Neural Computation, (7):219 (1995).

International Search Report for corresponding PCT application No. PCT/US17/21736, dated Jun. 30, 2017.

Srivastava, "Improving Neural Networks with Dropout", Master's Thesis, Graduate Department of Computer Science, University of Toronto (2013).

Tian et al., "Hierarchical-TGDR: Combining biological hierarchy with a regularization method for multi-class classification of lung cancer samples via high-throughput gene-expression data", Systems Biomedicine, 1(4):278-287 (2013).

Tibshirani, "Regression Shrinkage and Selection via the Lasso", J.R. Statist. Soc. B, 58(1):267-288 (1996).

Tikhonov, "On the Stability of Inverse Problems", Comptes Rendu (Doklady) de l'Academie des Sciences de l'Urss, vol. XXXIX, No. 5 (1943).

* cited by examiner

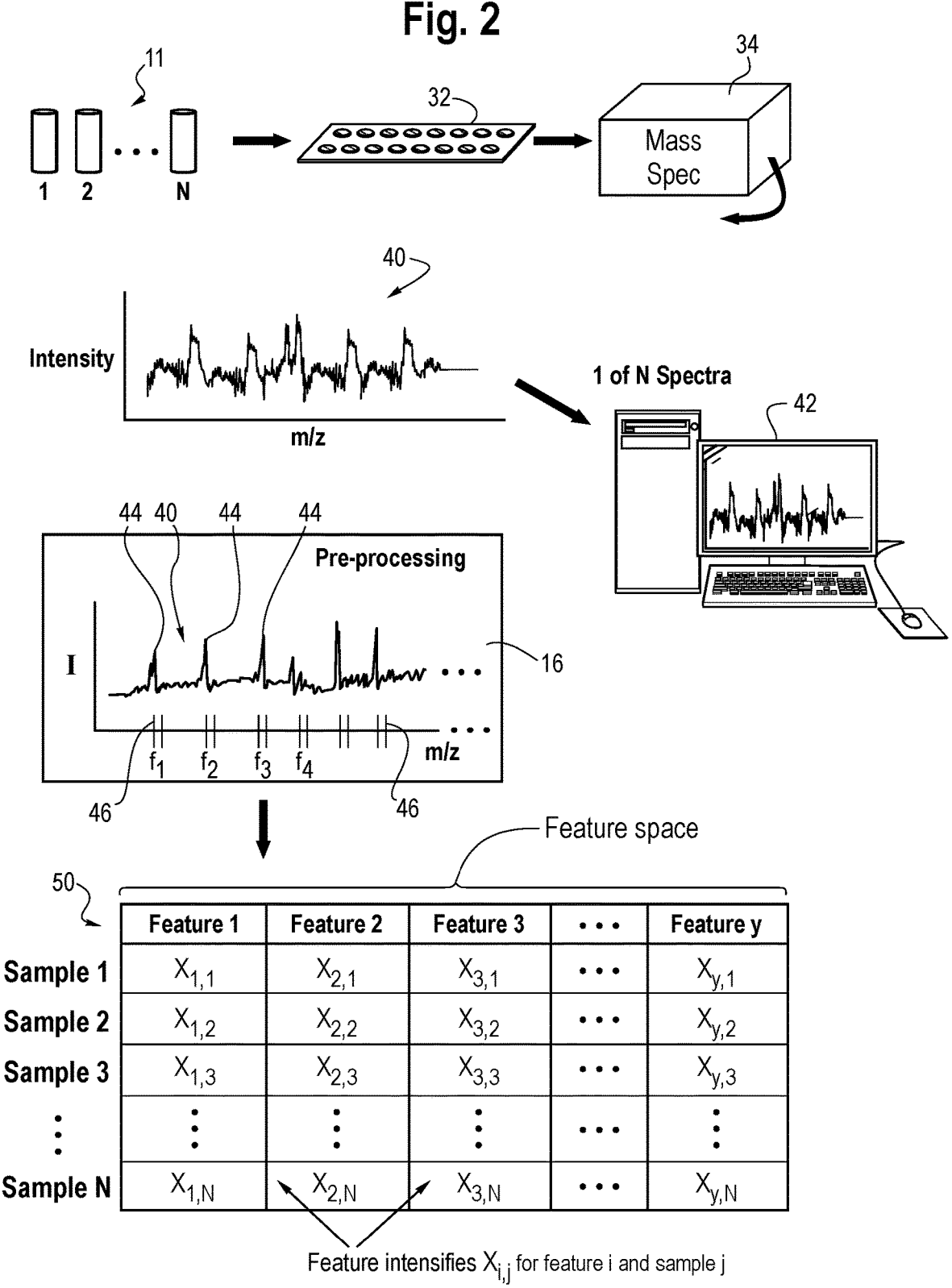

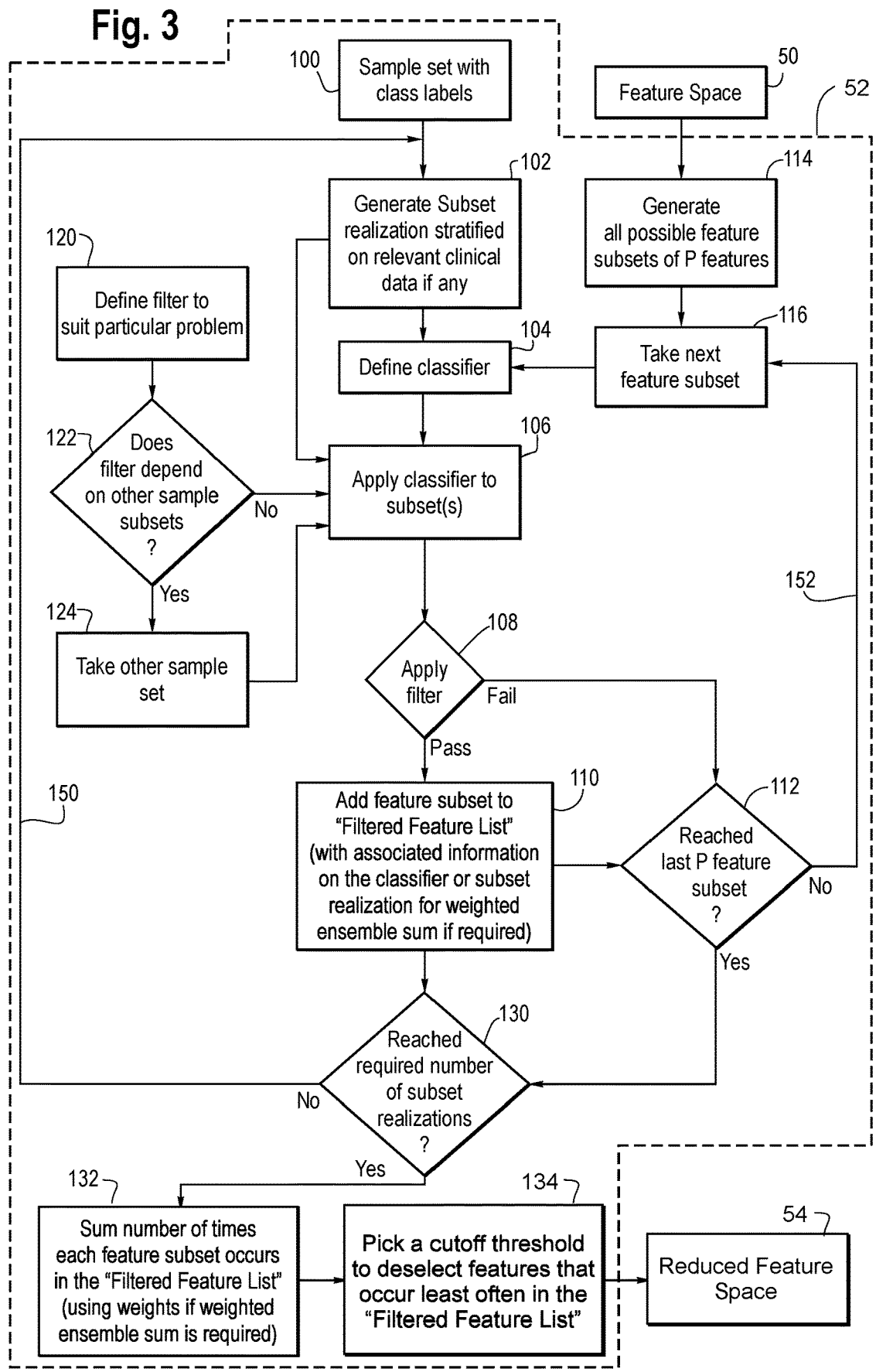

Fig. 4

Development Sample Set Realizations

| | Train | Remainder - Set Aside |
|---|---|---|
| Realization 1 | $S_1, S_3, S_5, ...$ | $S_2, S_4, S_6, ...$ |
| Realization 2 | $S_1, S_2, S_5, S_6, ...$ | $S_3, S_4, S_7, S_8, ...$ |
| Realization 3 | $S_1, S_2, S_3, S_7,$ $S_8, S_9, ...$ | $S_4, S_5, S_6,$ $S_{10}, S_{11}, S_{12}, ...$ |
| Realization 4 | $S_1, ... S_{10}$ $S_{21}, ... S_{30}, ...$ | $S_{11}, ... S_{20}$ $S_{31}, ... S_{40}, ...$ |
| ⋮ | ⋮ | ⋮ |
| Realization M | $S_1, ... S_{N/2}$ | $S_{N/2+1}, ... S_N$ |

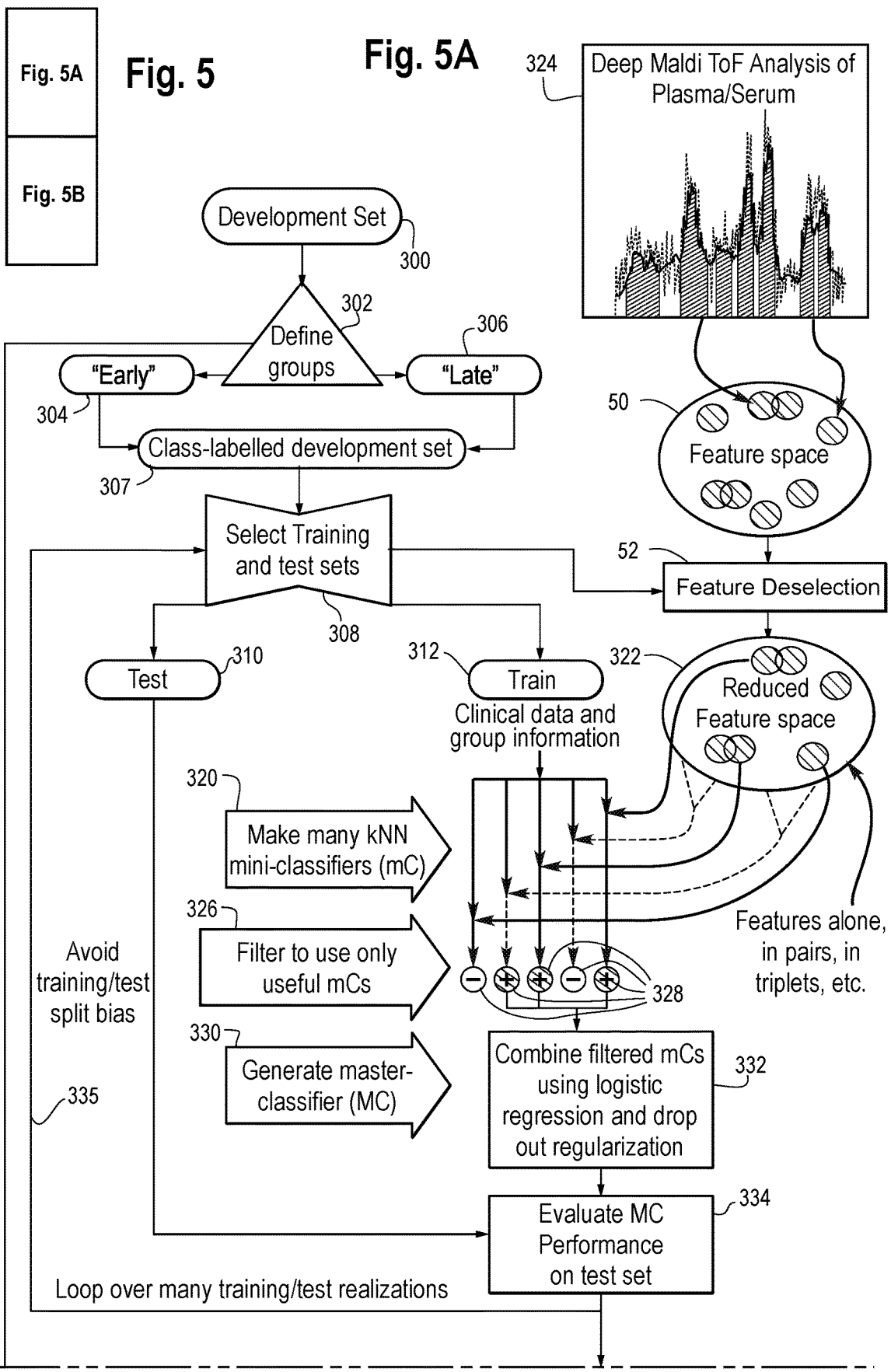

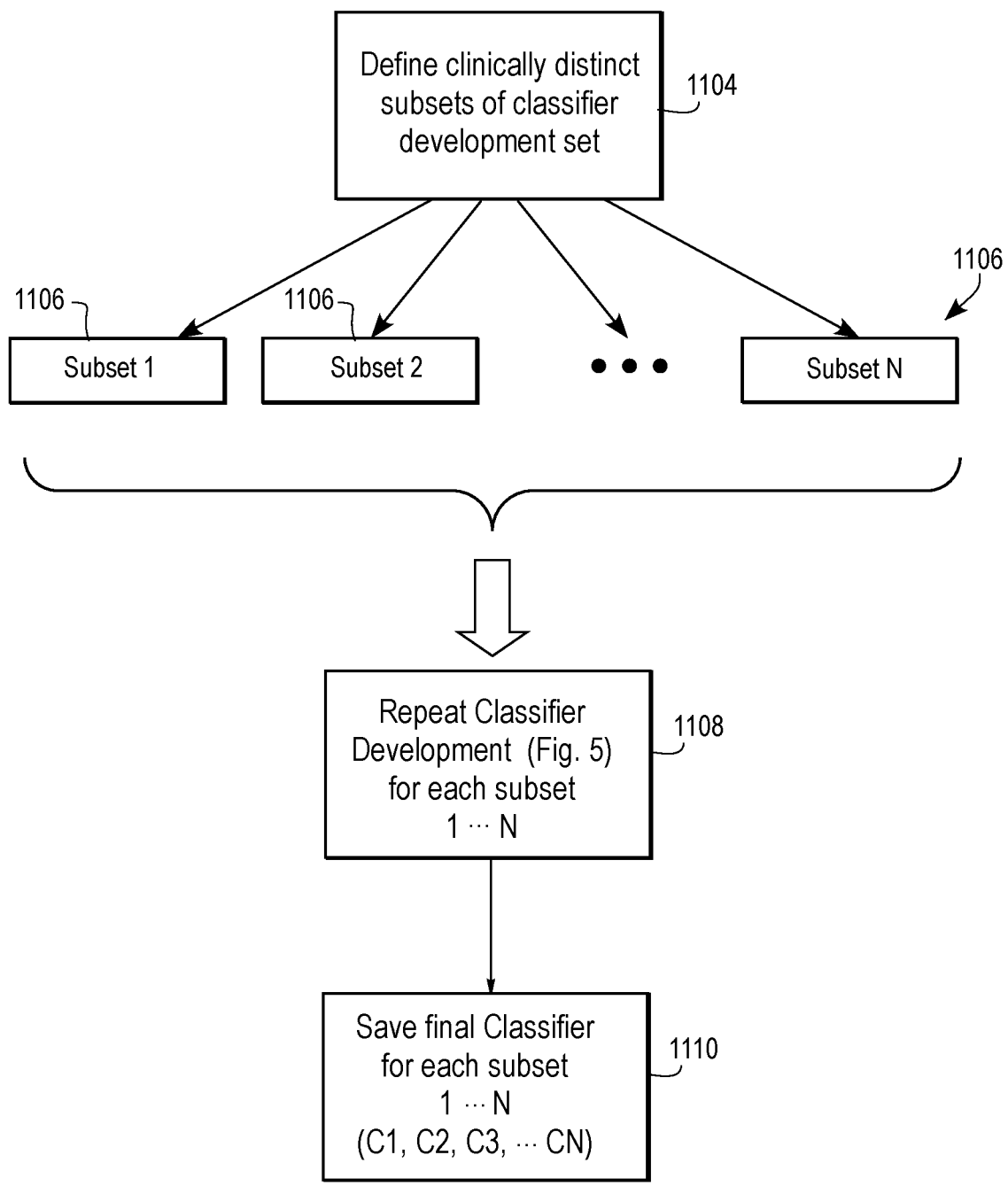

CLASSIFIER GENERATION METHODS AND PREDICTIVE TEST FOR OVARIAN CANCER PATIENT PROGNOSIS UNDER PLATINUM CHEMOTHERAPY

PRIORITY

This application is a Section 371 national phase application of PCT/US2017/021736, filed Mar. 10, 2017, which claims the benefit of U.S. provisional application Ser. No. 62/319,958 filed Apr. 8, 2016, contents of which are both incorporated by reference, including appendices thereof.

FIELD

This disclosure relates to the field of biomarker discovery and methods of generating classifiers which are useful for making predictions of patient benefit of drugs or prognosis. Examples are described of generating classifiers guiding treatment of ovarian cancer patients.

BACKGROUND

A classifier is a programmed computer that takes an input set of data (typically measurement data from a sample, e.g., blood sample) and generates a class label for the sample with the aid of a classification algorithm, such as k nearest neighbors, a margin-based classification algorithm, decision tree, support vector machine, etc., and a stored set of training or reference data of the same type as the measurement data of the test sample. The class label assigned by the classifier may take the form of a label in a binary classification scheme, such as Good/Poor, Benefit/Non-Benefit, Cancer/Non-Cancer, Early/Late, etc., and is typically associated with a clinical question being answered by the classifier.

Ovarian cancer is relatively rare, representing only 1.3% of all new cancer cases in the United States. However, most ovarian cancers are diagnosed once they have metastasized and then five year survival is only 28%. (NCI: Surveillance, Epidemiology and End Results program, http://seer.cancer.gov/statfacts/html/ovary.html). The main primary therapy for patients with advanced ovarian cancer is surgery followed by chemotherapy, usually platinum-based. (NCCN Guidelines Version 2.2015 Epithelial Ovarian Cancer/Fallopian Tube Cancer/Primary Peritoneal Cancer). The initial response to platinum-based chemotherapy can be divided into three categories: platinum-refractory (patients do not respond to therapy and demonstrate progression while on chemotherapy), platinum-resistant (patients progress within six months of completion of the chemotherapy) and platinum-responsive.

Platinum-based chemotherapy drugs, including cisplatin cis-$PtCl_2(NH_3)_2$) and analogs thereof, are used to treat various kinds of cancers, including sarcomas, lymphomas, and carcinomas. The drug reacts in vivo, binding to and causing crosslinking of, which interferes with cell division by mitosis, ultimately triggering apoptosis (programmed cell death). Cisplatin combination therapy is a cornerstone of treatment of many cancers. However, while initial platinum responsiveness is high, some patients do not respond to treatment, and the majority of cancer patients will eventually relapse with cisplatin resistant disease.

The applicant's assignee, Biodesix, Inc., has developed a test known as VeriStrat, which was developed to guide treatment of Non-Small Cell Lung Cancer (NSCLC) patients. The test is described in U.S. Pat. No. 7,736,905, the content of which is incorporated by reference herein. In brief the VeriStrat test is based on serum and/or plasma samples of cancer patients. Through a combination of matrix assisted laser desorption/ionization time of flight (MALDI-TOF) mass spectrometry and data analysis algorithms implemented in a computer, the commercial version of the test includes a classifier which compares a set of eight integrated peak intensities at predefined m/z ranges in the mass spectrum of the patient sample (after pre-processing steps are performed) with those from a training cohort, and generates a class label for the patient sample using a k nearest neighbor algorithm: either VeriStrat Good, VeriStrat Poor, or VeriStrat "indeterminate." In multiple clinical validation studies it has been shown that patients, whose pre-treatment serum/plasma is classified as VeriStrat Good, have significantly better outcome when treated with epidermal growth factor receptor inhibitor drugs than those patients whose sample is classified as VeriStrat Poor. In a few cases (less than 2%) no determination can be made, resulting in a VeriStrat indeterminate label.

The applicants have further discovered that the VeriStrat test is also predictive for whether head and neck squamous cell carcinoma and colorectal cancer patients are likely to have better or worse outcomes from treatment with certain anti-cancer drugs, as described in U.S. Pat. Nos. 8,024,282; 7,906,342; 7,879,620; 7,867,775; 7,858,390; 7,858,389 and 7,736,905.

U.S. Pat. No. 8,718,996, also assigned to Biodesix, Inc., describes methods of predicting whether ovarian cancer patients are likely or not to benefit from platinum chemotherapies using the VeriStrat test.

Our recent work in classifier development described in this document has led to new and improved classifiers which are able to predict whether an ovarian cancer patient is exceptionally unlikely to benefit from platinum-based chemotherapy, or is alternatively likely to perform exceptionally well on platinum-based chemotherapy. The classifier and tests described in this document differ in many ways from the classifier described in the '996 patent, including it is derived from a different class of patients, it is based on a much deeper probing of the biomarker content of a blood-based sample, uses different mass spectral peaks for performing classification of a sample, was developed using a completely different classifier generation process, and includes in preferred embodiments a multi-tiered or hierarchical classifier construction to generate one of three different possible class labels for a sample, two of which identify patients which are likely to have exceptionally good or exceptionally bad prognosis on platinum chemotherapies. Accordingly, the present classifiers and tests described in this document are considered to be a new and nonobvious improvement over the classifier and test described in the '996 patent.

SUMMARY

In one aspect, a classifier generation method is described, including the steps of:

a) obtaining physical measurement data from a development set of samples and supplying the measurement data to a general purpose computer, each of the samples further associated with clinical data;

b) identifying a plurality of different clinical sub-groups 1 . . . N within the development set based on the clinical data;

c) for each of the different clinical sub-groups, conducting a classifier generation process from the measurement data for each of the members of the development set that is associated with such clinical sub-groups, thereby generating clinical sub-group classifiers C1 . . . CN; and d) storing in memory of a computer a classification procedure involving all of the classifiers C1 . . . CN developed in step c), each of the classifiers associated with a reference set comprising samples in the development set used to generate the classifier and associated measurement data.

In another aspect, a multi-stage classifier is disclosed which includes a programmed computer implementing a hierarchical classifier construction operating on mass spectral data of a test sample stored in memory and making use of a reference set of class-labeled mass spectral data stored in the memory. The classifier includes (a) a first stage classifier for stratifying the test mass spectral data into either an Early or Late group (or the equivalent, the moniker not being important); (b) a second stage classifier for further stratifying the Early group of the first stage classifier into Early and Late groups (or Earlier and Later groups, or the equivalent), the second stage implemented if the first stage classifier classifies the test mass spectral data into the Early group and the Early class label produced by the second stage classifier is associated with an exceptionally poor prognosis; and (c) a third stage classifier for further stratifying the Late group of the first stage classifier into Early and Late groups (or Earlier and Later groups, or the equivalent). The third stage classifier is implemented if the first stage classifier classifies the test mass spectral data into the Late group, wherein a Late class label (or Later or the equivalent) produced by the third stage classifier is associated with an exceptionally good prognosis.

In yet another aspect, we have discovered a method of generating a classifier for classifying a test sample from a development set of samples, each of the samples being associated with clinical data. The method includes the steps of:

(a) dividing the development set of samples into different clinical subgroups 1 . . . N based on the clinical data, where N is an integer of at least 2;

(b) performing a classifier development process (such as for example the process of FIG. 5) for each of the different clinical subgroups 1 . . . N, thereby generating different classifiers C1 . . . CN; and (c) defining a final classification process whereby a patient sample is classified by the classifiers C1 . . . CN.

In still another aspect, we have discovered a method of generating a classifier for classifying a test sample, comprising the steps of:

(a) generating a first classifier from measurement data of a development set of samples using a classifier development process;

(b) performing a classification of the measurement data of the development set of samples using the first classifier, thereby assigning each member of the development set of samples with a class label in a binary classification scheme (Early/Late, or the equivalent); and (c) generating a second classifier using the classifier development process with an input classifier development set being the members of the development set assigned one of the two class labels in the binary classification scheme by the first classifier (e.g., the Early group), the second classifier thereby stratifying the members of the set with the first class label into two fluffier sub-groups. The method optionally includes the steps (d) dividing the development set of samples into different clinical subgroups 1 . . . N where N is an integer of at least 2; (repeating the classifier development process for each of the different clinical subgroups 1 . . . N, thereby generating different third classifiers C1 . . . CN; and (f) defining a hierarchical classification process whereby:

i. a patient sample is classified first by the first classifier generated in step a);

ii. if the class label assigned by the first classifier is the class label used to generate the second classifier, then classifying the patient sample with the second classifier; and iii. if the class label assigned by the first classifier is not the class label used to generate the second classifier, then classifying the patient sample with the third classifiers C1 . . . CN: and iv, assigning a final label as a result of classification steps ii or step iii.

This document discloses an example of the development of classifiers which predict in advance whether an ovarian cancer patient is likely to be platinum-refractory or platinum-resistant in treatment of the ovarian cancer with platinum-based chemotherapy, in one embodiment, the classifier includes: a) a machine-readable memory storing a reference set of class-labeled mass spectral data obtained from blood-based samples of other ovarian cancer patients treated with the platinum-based chemotherapy. The mass spectral data is in the form of a feature table of intensity values of a multitude of mass spectral features. The class labels are of the form Early or the equivalent, indicating that the sample was from a patient who did relatively poorly on platinum-based chemotherapy, or Late or the equivalent, indicating that the sample was from a patient that did relatively well on platinum-based chemotherapy. The classifier also includes h) a programmed computer implementing a classification algorithm comparing mass spectral data of a sample to be tested with the reference set and generating a class label for the sample to be tested.

In particular, the classification algorithm implements a hierarchical multi-level classification in series including classification at at least a first level ("Classifier A" in the following description) and a second level ("Classifier B" in the following description). The classification algorithm at the first level produces a class label of Early or Late or the equivalent. The class label Late or the equivalent identifies patients as being likely to not be platinum-refractory or platinum-resistant in treatment of the ovarian cancer with platinum-based chemotherapy. If the class label assigned at the first level is Early or the equivalent, the classification algorithm proceeds to the second level. The classifier at the second level uses a subset of the reference set in the fibrin of patients identified with the class label Early or the equivalent further stratified into Early and Late class labels (or Earlier or Later labels, or the equivalent). The classification algorithm at the second level generates a class label of Bad or the equivalent identifying patients as likely to perform very poorly on platinum-based chemotherapy, i.e., be platinum-refractory or platinum-resistant.

In one embodiment, the hierarchical multi-level classification includes a third classification level ("Classifier C" in the following description), wherein a class label assigned at the third classification level is used to identify patients as being likely to have particularly good outcomes on the platinum-based chemotherapy, and is applied to those samples which are assigned the Late (or equivalent) class label by the first level classifier.

We have found that is desirable to develop classifiers from different clinical sub-groups within a classifier development set used to generate the first level classifier. For example, the classifiers at the third classification level can be developed from one or more different clinical subgroups, for example four different classifiers C1, C2, C3, and C4, each developed from the different clinical sub-groups. In the ovarian cancer scenario, these clinical subgroups can take the form of: C1: a subset of patients with non-serous histology or serous histology together with unknown FIGO (a cancer scoring system) score; C2: a subset of patients not used to develop Classifier C1 (e.g., patients with serous histology and known FIGO score); C3: a subset of patients with residual tumor after surgery; C4: a subset of patients with no residual tumor after surgery.

These and other aspects of the invention will be described with greater detail in the following description and with reference to the appended drawings.

BRIEF DESCRIPTION OF THE DRAWINGS

FIG. 2 is a flow diagram showing the process steps for taking a set of N blood-based samples (in this example from ovarian cancer patients in advance of treatment with platinum chemotherapy), generating mass spectral data from the blood samples, pre-processing the spectra in a computer and generating a table of y mass spectrometry feature values for each of the samples (referred to herein as a feature space) as preliminary steps for generating the measurement data to start a classifier development exercise.

FIG. 3 is a flow chart of a bagged feature selection/deselection outline which is performed in the process shown in FIG. 2A.

FIG. 4 is an illustration of M different development sample set realizations which are used in the bagged feature selection/deselection routine of FIG. 3.

FIGS. 5A and 5B are a flow chart showing a computer-implemented procedure for developing a classifier from a development sample set, e.g., the development set of samples shown in FIG. 2. The procedure of FIGS. 5A and 5B (up to and including step 350) was performed several different times for different configurations or subsets of the development sample set to result in the creation of a tiered or hierarchical series of classifiers (referred to as Classifiers A, B and C), as will be explained in more detail in the detailed description.

FIG. 6A shows the plot of DFS; FIG. 6B shows the plot for OS. Note that the plots for the development and validation sample sets are essentially the same.

FIG. 7A is a plot of OS for the development set; FIG. 7B is a plot of DFS for the development set; FIG. 7C is a plot of OS for the validation set; FIG. 7D is a plot of DFS for the validation set.

FIGS. 10A and 109 are Kaplan-Meier plots of OS and DFS, respectively, by classification group produced by the Classifier B classifier, for the subset of the development set of samples which were used to develop the Classifier B.

FIG. 11 is a flow chart showing a process for generating a third tier classifier C; in this particular example the third tier consists of a several different classifiers each based on a different and clinically distinct subset of the development sample set.

DETAILED DESCRIPTION

The classifier generation methods of this disclosure will be illustrated in the following example of a development of a classifier (actually, several classifiers) which are capable of identifying, in advance of treatment, whether an ovarian cancer patient is likely to be platinum-refractory or platinum-resistant in treatment of the cancer with platinum chemotherapy. Embodiments are disclosed in which the classifier is able to identify patients that are likely to obtain particular benefit from platinum chemotherapy, as well as patients that are likely to perform extremely poorly on the platinum chemotherapy.

While the present disclosure provides one specific example of the development of a classifier using the inventive methods, it will be appreciated that the method of classifier development is of general applicability to other types of cancers or other types of treatments, and therefore the ovarian cancer/platinum chemotherapy example is offered by way of example and not limitation. Additionally, while the present example uses mass spectrometry data to develop a classifier, in principle the methods are applicable to other types of data sets such as genomic or proteomic data.

Figure 2A:
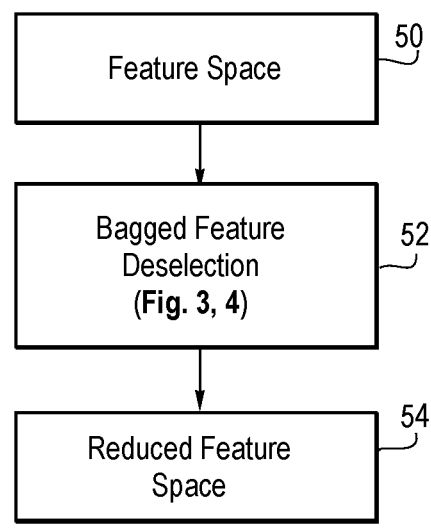
FIG. 2A is a flow chart showing the steps for reducing the set of features identified initially using the process of FIG. 2 to a more reduced set of features used as part of the classifier development exercise.

In the following description, we will first describe the samples used in the ovarian classifier development effort, the physical and computer processing operations, including sample preparation and mass spectrometry spectral acquisition, to obtain measurement data from the samples (see FIG. 2), and a filtering process we refer to as "bagged filtering" we used to reduce the set of possible candidate features for classification to a smaller set with greater classification power (see FIGS. 2A, 3, 4). The classifier generation methodology we used is known as "Combination of Mini-Classifiers with Drop-out Regularization", or CMC/D, which is described in detail in FIGS. 5A and 5B. This methodology, and rationale, is explained in detail in U.S. patent application publication 2015/0102216 of H. Roder et al., the content of which is incorporated by reference herein, and will be described in some detail below. Performance of the classifiers we generated is described in FIGS. 7, 8, 10 and 16. FIGS. 9 and 11-14 and the accompanying discussion will explain how and why we generated multi-level hierarchical classifiers. FIG. 15 illustrates a practical testing environment for testing a blood-based sample using the classifiers of this disclosure.

Samples

A set of 165 blood-based (serum) samples from an observational trial of patients with ovarian cancer were available. Patients underwent surgery followed by platinum-based chemotherapy. Samples were taken at the time of surgery (in advance of treatment with platinum-based chemotherapy). Of the 165 patients, 23 did actually not start chemotherapy, were not newly diagnosed, or had received prior therapy for ovarian cancer. Outcome data was not available for an additional four patients. Data are presented here for the remaining 138 patients. The most important baseline clinical data available for these patients are summarized in table 1. Note: two patients of the 138 did not have disease-free survival data available.

TABLE 1

Baseline characteristics of patients with available outcome data

| | | n (%) |
|---|---|---|
| Histology | serous | 100 (72) |
| | non-serous | 38 (28) |
| VeriStrat Label | Good | 110 (80) |
| | Poor | 27 (20) |
| | Indeterminate | 1 (1) |
| FIGO | NA | 39 (29) |
| | 1 | 13 (9) |
| | 2 | 3 (2) |
| | 3 | 54 (39) |
| | 4 | 29 (21) |
| Histologic Grade | NA | 2 (1) |
| | 1 | 7 (5) |
| | 2 | 53 (38) |
| | 3 | 76 (55) |
| Metastatic Disease | yes | 20 (14) |
| | no | 118 (86) |
| Residual Tumor | yes | 53 (38) |
| | no | 85 (62) |
| Age | Median (range) | 59 (18-88) |

Figure 1A:
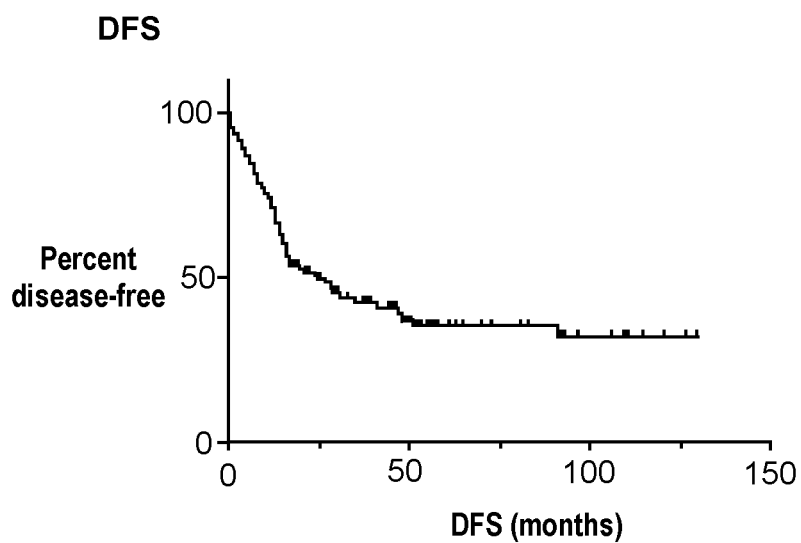
FIGS. 1A and 1B are Kaplan-Meier plots of time to event data for disease free survival (DFS, FIG. 1A) and overall survival (OS) for a cohort of 138 ovarian cancer patients with available clinical data and mass spectral data, which were used to develop the classifiers of this disclosure.
Figure 1B:
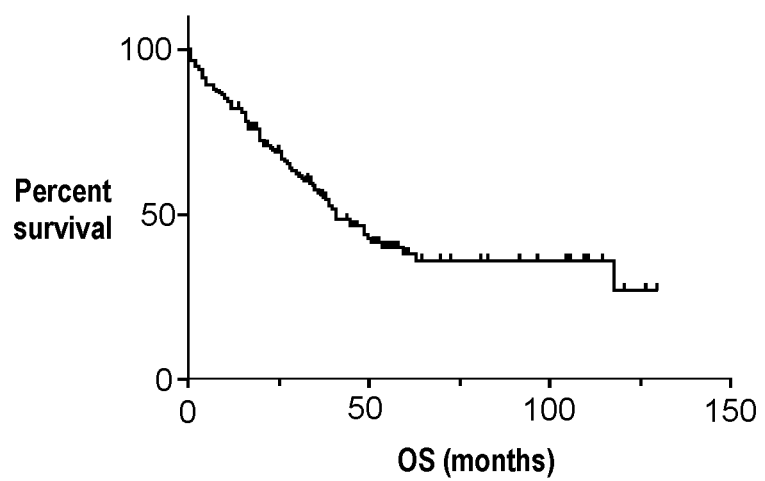

Kaplan-Meier plots for disease-free-survival (DFS) and overall survival (OS) for the cohort of 138 patients with baseline samples and acquired spectra are shown in FIG. 1.

Sample Preparation Serum samples were thawed and 3 µl aliquots of each experimental sample (from patients with ovarian cancer) and quality control serum (a pooled sample obtained from serum of five healthy patients, purchased from ProMedDx, "SerumP3") were spotted onto VeriStrat® cellulose serum cards (Therapak). The cards were allowed to dry for 1 hour at ambient temperature after which the whole serum spot was punched out with a 6 mm skin biopsy punch (Acuderm). Each punch was placed in a centrifugal filter with 0.45 µm nylon membrane (VWR). One hundred µl of HPLC grade water (JT Baker) was added to the centrifugal filter containing the punch. The punches were vortexed gently for 10 minutes then spun down at 14,000 rcf for two minutes. The flow-through was removed and transferred back on to the punch for a second round of extraction. For the second round of extraction, the punches were vortexed gently for three minutes then spun down at 14,000 rcf for two minutes. Twenty microliters of the filtrate from each sample was then transferred to a 0.5 ml eppendorf tube for MALDI analysis.

All subsequent sample preparation steps were carried out in a custom designed humidity and temperature control chamber (Coy Laboratory). The temperature was set to 30° C. and the relative humidity at 10%.

An equal volume of freshly prepared matrix (25 mg of sinapinic acid per 1 ml of 50% acetonitrile: 50% water plus 0.1% TFA) was added to each 20 µl serum extract and the mix vortexed for 30 sec. The first three aliquots (2×2 µl) of sample:matrix mix were discarded into the tube cap. Eight aliquots of 2 µl sample:matrix mix were then spotted onto a stainless steel MALDI target plate (SimulTOF). The MALDI target was allowed to dry in the chamber before placement in the MALDI mass spectrometer.

This set of samples was processed for MALDI analysis in four batches. QC samples were added to the beginning (two preparations) and end (two preparations) of each batch run.

Acquisition of Measurement Data

As noted above, a physical measurement process is carried out on the biological samples obtained for classifier development. In one possible example, this measurement process is MALDI-TOF mass spectrometry. The samples could also be subject to two or more different measurement processes, e.g., mass spectrometry and genomic or proteomic assay, etc. (It will be noted that the use of two different samples from a single patient for measurement is considered equivalent to two measurements of the same physical sample.) As shown in FIG. 2, aliquots of the plasma or serum samples 11 are spotted onto one or more spots of a MALDI-TOF plate 32 and the plate 32 is inserted into a MALDI-TOF mass spectrometer 34. Mass spectrometry is performed on the aliquot(s) and the resulting mass spectrum 40 (or spectra) are generated and stored in the MALDI-TOF mass spectrometer 34. In one possible embodiment this step could take the form of acquisition of Deep MALDI spectra in accordance with the teachings disclosed in U.S. patent application Ser. No. 13/836,436 filed Mar. 15, 2013, now U.S. Pat. No. 9,279,798, the content of which is incorporated by reference.

The mass spectrometry data is supplied to general purpose computer 42 (FIG. 2) equipped with software (known) for analyzing and displaying the spectra. One such spectrum is shown in FIG. 2 at 40, which consists of a plot of intensity (I) as a function of mass/charge ratio (m/z) as is conventional in the art. Spectrum 40 (or a multitude of spectra) are obtained from each sample and supplied to the computer 42.

A pre-processing step is performed in the computer 42 of FIG. 2. The pre-processing includes an averaging function to produce a single average spectrum from a multitude of spectra obtained from each sample. The pre-processing also identifies peaks in the spectra which may be useful for classification, and obtains integrated intensity values of m/z ranges associated with such peaks. The pre-processing can include steps of background subtraction, normalization of spectra, and alignment of spectra in order to result in a spectrum for use to identify peaks and measure intensity of features or peaks in the spectra. Such pre-processing is known in the art and described in U.S. Pat. No. 7,736,905, the content of which is incorporated by reference herein. In FIG. 2, such peaks or features in the spectrum 40 are shown at 44. The m/z ranges are shown at 46 for each of such peaks. These m/z ranges correspond to a number of different features f1, f2, f3, . . . fy. The number of features, y, which are potentially useful for generating a classifier, could be on the order of 50, 100 or potentially much larger, such as 500 or more using the techniques of the Deep MALDI application described above.

The pre-processing step 16 obtains integrated intensity values for the m/z range 46 for each of the features f1, f2, f3 . . . fy and stores this information in a table 50, shown in FIG. 2, of intensity value for each feature. Such a table 50 includes the integrated intensity values for each feature for all N samples in the development sample set 11 of FIG. 2. The collection of features is sometimes referred to as "feature space" in the following discussion.

Spectral Acquisition

MALDI spectra were obtained using a MALDI-TOF mass spectrometer (SimulTOF 100 s/n: LinearBipolar 11.1024.01 from Virgin Instruments, Sudbury, Mass., USA). The instrument was set to operate in positive ion mode, with ions generated using a 349 nm, diode-pumped, frequency-tripled Nd:YLF laser operated at a laser repetition rate of 0.5 kHz. External calibration was performed using a mixture of standard proteins (Bruker Daltonics, Germany) consisting of insulin (m/z 5734.51 Da), ubiquitin (m/z, 8565.76 Da), cytochrome C (m/z 12360.97 Da), and myoglobin (m/z 16952.30 Da).

Spectra from each MALDI spot (8 spots per sample) were collected as 800 shot spectra that were 'hardware averaged' as the laser fires continuously across the spot while the stage is moving at a speed of 0.25 mm/sec. A minimum intensity threshold of 0.01 V was used to discard any 'flat line' spectra. All 800 shot spectra with intensity above this threshold were acquired without any further processing.

MALDI-TOF mass spectral data acquisition and processing (both for purposes of acquiring a set of data for classifier development and to perform a test on a sample for patient benefit) is optionally performed in accordance with the so-called "Deep MALDI" method described in published patent application of H. Röder et al., U.S. Pat. No. 9,279,798, the content of which is incorporated by reference herein. This '798 patent describes the surprising discovery that collecting and averaging large numbers of laser shots (typically 100,000 to 500,000 or more) from the same MALDI spot or from the combination of accumulated spectra from multiple spots of the same sample, leads to a reduction in the relative level of noise vs. signal and that a significant amount of additional spectral information from mass spectrometry of complex biological samples is revealed. The document also demonstrates that it is possible to run hundreds of thousands of shots on a single spot before the protein content on the spot is completely depleted. Second, the reduction of noise via averaging many shots leads to the appearance of previously invisible peaks (i.e., peaks not apparent in spectra resulting from typical 1,000 laser shots). Even previously visible peaks become better defined and allow for more reliable measurements of peak intensity and comparisons between samples when the sample is subject to a very large number of shots. The classifier of this disclosure takes advantage of the deep MALDI method to look deep into the proteome of serum samples and uses relatively large numbers of peaks for classification which would not be otherwise observable in conventional "dilute and shoot" spectra obtained from the typical ~1000 shot mass spectrum. In the present classification exercise, we used the Deep MALDI method in order to look deep into the serum proteome and identified a large number of peaks (hundreds) for classification. We then filtered this list of peaks down using the "bagged filtering" process described below.

The following section of this document describes the spectral processing we used on the raw spectra from the mass spectrometer in order to construct a feature table for use in classifier generation. The following procedures are executed in software in a general purpose computer which receives the spectra from the mass spectrometer. Some of the steps, such as for example defining the features used for classification, may be performed in part or in whole by a human operator by inspection of plots of the mass spectral data.

Spectral Processing

Raster Spectra Preprocessing

Rescaling

Instrument calibration can introduce dramatic drifts in m/z, most apparent in the high mass region, by batch. This results in an inability to consistently use predefined workflows to process the data that rely on the position of peaks and a set tolerance for alignment. To overcome the problem, rescaling of the m/z data can be performed requiring a standard reference spectrum. The standard is compared to spectra from the current batch to identify if there is a shift in the position of common serum peaks. The m/z position is borrowed from the reference and any 'shift' applied to rescale the spectra. The results are rescaled spectra with comparable m/z across batches. In a sense, this is a batch correction procedure for gross alignment issues.

Alignment and Filtering

This workflow performs the ripple filter as it was observed that the resulting averages were improved in terms of noise. The spectra are then background subtracted and peaks are found in order to perform alignment. The spectra that are used in averaging are the aligned ripple filtered spectra without any other preprocessing. The calibration step uses a set of 43 alignment points listed below in table 3. Additional filtering parameters required that the spectra have at least 20 peaks and used at least 5 of the alignment points.

TABLE 3

Alignment points used to align the raster spectra

| m/z |
| --- |
| 3168 |
| 4153 |
| 4183 |
| 4792 |
| 5773 |
| 5802 |
| 6433 |
| 6631 |
| 7202 |
| 7563 |
| 7614 |
| 7934 |
| 8034 |
| 8206 |
| 8684 |
| 8812 |
| 8919 |
| 8994 |
| 9133 |
| 9310 |
| 9427 |
| 10739 |
| 10938 |
| 11527 |
| 12173 |

TABLE 3-continued

Alignment points used to align the raster spectra m/z 12572
12864
13555
13763
13882
14040
14405
15127
15263
15869
17253
18630
21066
23024
28090
28298
33500
67150

Raster Averaging

Averages were created from the pool of rescaled, aligned, and filtered raster spectra. A random selection of 500 spectra was averaged to create a final sample spectrum of 400,000 shots. We collected multiple 800 shot spectra per spot, so that we end up with a pool in excess of 500 in number of 800 shot raster spectra from the 8 spots from each sample. We randomly select 500 from this pool, which we average together to a final 400,000 shot average deep MALDI spectrum.

We further performed deep MALDI average spectra pre-processing, including background estimation and subtraction, normalization by bin method, average spectra alignment, a batch correction process, and partial ion current normalization. All of these details are not particularly important to the classifier generation methods of this disclosure and so are omitted for the sake of brevity and clarity. The interested reader is directed to the U.S. provisional patent application Ser. No. 62/289,587 filed Feb. 1, 2016, J. Roder et al. inventors, which sets forth these details. The '587 provisional application is incorporated by reference herein.

The above process resulted in the identification of approximately 350 mass spectral features which were potentially useful for classification (feature space 50). As shown in FIG. 2A, we performed a deselection process to further narrow the list of features to a smaller set of features which have the greatest classification power. See Table 18. In particular, we performed a bagged feature deselection process 52 (shown in detail in FIGS. 3 and 4), which resulted in a reduced features space 54 (322 in FIG. 5A), and this reduced feature space was then used in the classifier development (described in FIGS. 5A and 5B). This is described in detail below in conjunction with FIG. 5A in relationship with the classifier generation methodology we used.

Classifier Development

Figure 5B:
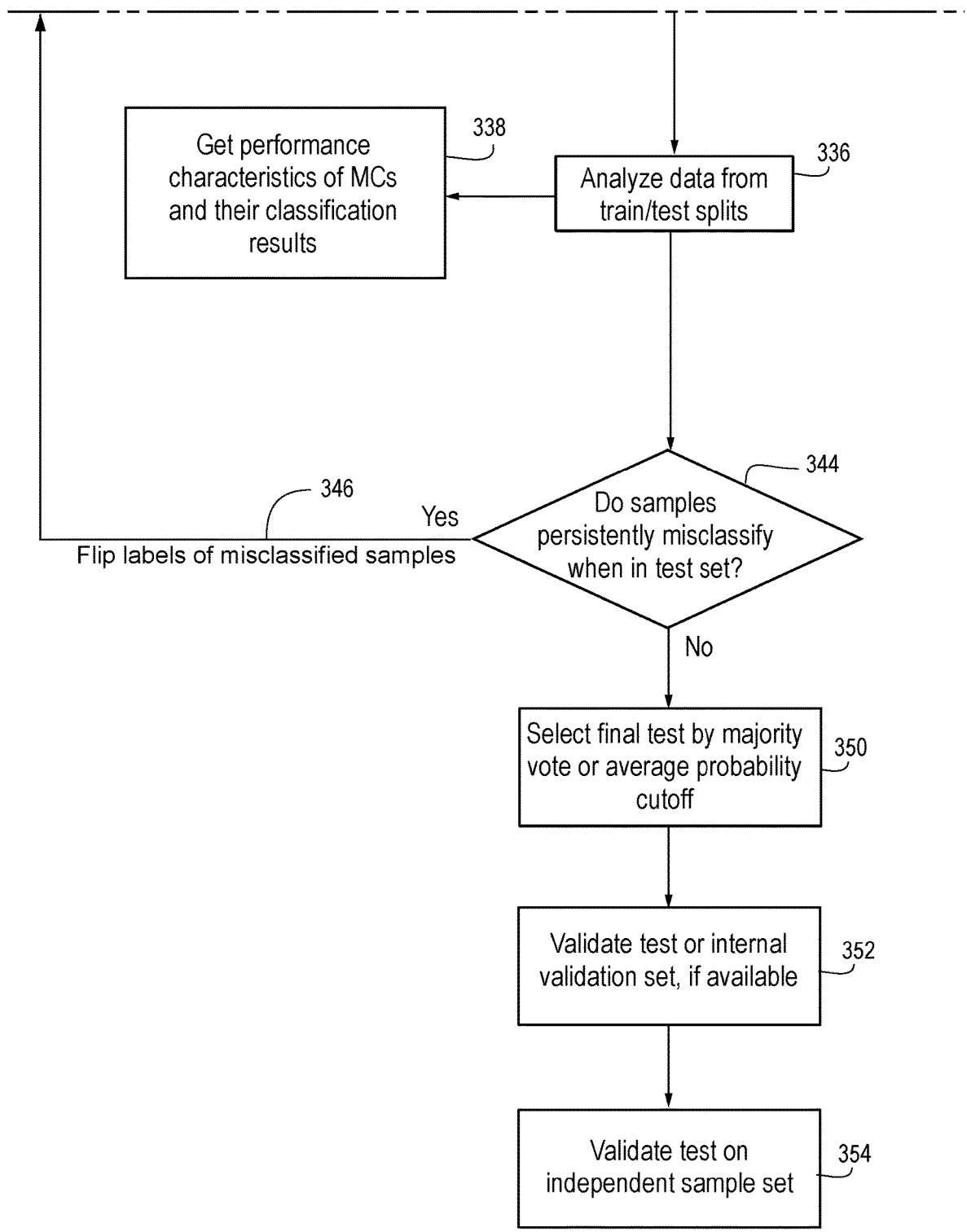

After the feature table for features in the mass spectra for the 138 samples was created (as explained above), we proceeded to develop a classifier for ovarian cancer patient prognosis on platinum chemotherapy using the classifier generation method shown in flow-chart form in FIGS. 5A and 5B. This method, known as "combination of mini-classifiers with drop-out regularization" or "CMC/D", or DIAGNOSTIC CORTEX™, is described at length in the U.S. Pat. No. 9,477,906 of H. Röder et al., the entire content of which is incorporated by reference herein. An overview of the methodology and how it is combined with the method of bagged feature deselection (or bagged filtering) will be provided here first, and then illustrated in detail in conjunction with FIGS. 5A and 5B for the generation of the ovarian/platinum chemotherapy classifier.

In contrast to standard applications of machine learning focusing on developing classifiers when large training data sets are available, the big data challenge, in bio-life-sciences the problem setting is different. Here we have the problem that the number (n) of available samples, arising typically from clinical studies, is often limited, and the number of attributes (measurements) (p) per sample usually exceeds the number of samples. Rather than obtaining information from many instances, in these deep data problems one attempts to gain information from a deep description of individual instances. The present methods take advantage of this insight, and are particularly useful, as here, in problems where $p \gg n$.

The method includes a first step a) of obtaining measurement data for classification from a multitude of samples, i.e., measurement data reflecting some physical property or characteristic of the samples. The data for each of the samples consists of a multitude of feature values, and a class label. In this example, the data takes the form of mass spectrometry data, in the form of feature values (integrated peak intensity values at a multitude of m/z ranges or peaks) as well as a label indicating some attribute of the sample (for example, patient Early or Late death or disease progression). In this example, an initial guess of the class labels was assigned by a human operator to each of the samples after investigation of the clinical data associated with the sample. The development sample set is then split into a training set and a test set and the training set is used in the following steps b), c), d), and e).

The method proceeds with a step b) of using bagged feature deselection (bagged filtering) to reduce the feature space assessed in step a) by discarding features that show no consistent utility for the classification problem being addressed. This method is described in more detail in the following section. The bagged feature deselection process reduces the whole feature space evaluated in step a) (50 in FIG. 2) to a smaller subset of the feature space, the reduced feature space (54 in FIG. 2A and FIG. 3), by discarding features or combinations of features that show no consistent utility for sample classification.

The method continues with a step c) of constructing a multitude of individual mini-classifiers using sets of feature values from the samples up to a pre-selected feature set size s (s=integer 1 . . . n) from the reduced feature space. For example a multiple of individual mini- or atomic classifiers could be constructed using a single feature (s=1), or pairs of features (s=2), or three of the features (s=3), or even higher order combinations containing more than 3 features. The selection of a value of s will normally be small enough to allow the code implementing the method to run in a reasonable amount of time, but could be larger in some circumstances or where longer code run-times are acceptable. The selection of a value of s also may be dictated by the number of measurement data values (p) in the data set, and where p is in the hundreds, thousands or even tens of thousands, s will typically be 1, or 2 or possibly 3, depending on the computing resources available. The mini-classifiers execute a supervised learning classification algorithm, such as k-nearest neighbors (kNN), in which the values for a feature, pairs or triplets of features of a sample instance are compared to the values of the same feature or features in a training set and the nearest neighbors (e.g., k=9) in an s-dimensional feature space are identified and by majority vote a class label is assigned to the sample instance for each mini-classifier. In practice, there may be thousands of such mini-classifiers depending on the number of features which are used for classification.

The method continues with a filtering step d), namely testing the performance, for example the accuracy, of each of the individual mini-classifiers to correctly classify the sample, or measuring the individual mini-classifier performance by some other metric (e.g. the difference between the Hazard Ratios (HRs) obtained between groups defined by the classifications of the individual mini-classifier for the training set samples) and retaining only those mini-classifiers whose classification accuracy, predictive power, or other performance metric, exceeds a pre-defined threshold to arrive at a filtered (pruned) set of mini-classifiers. The class label resulting from the classification operation may be compared with the class label for the sample known in advance if the chosen performance metric for mini-classifier filtering is classification accuracy. However, other performance metrics may be used and evaluated using the class labels resulting from the classification operation. Only those mini-classifiers that perform reasonably well under the chosen performance metric for classification are maintained. Alternative supervised classification algorithms could be used, such as linear discriminants, decision trees, probabilistic classification methods, margin-based classifiers like support vector machines, and any other classification method that trains a classifier from a set of labeled training data.

To overcome the problem of being biased by some univariate feature selection method depending on subset bias, we take a large proportion of all possible features as candidates for mini-classifiers. We then construct all possible KNN classifiers using feature sets up to a pre-selected size (parameter s). This gives us many "mini-classifiers": e.g. if we start with 100 features for each sample (p=100), we would get 4950 "mini-classifiers" from all different possible combinations of pairs of these features (s=2), 161,700 mini-classifiers using all possible combination of three features (s=3), and so forth. Other methods of exploring the space of possible mini-classifiers and features defining them are of course possible and could be used in place of this hierarchical approach. Of course, many of these "mini-classifiers" will have poor performance, and hence in the filtering step d) we only use those "mini-classifiers" that pass predefined criteria. These filtering criteria are chosen dependent on the particular problem: If one has a two-class classification problem, one would select only those mini-classifiers whose classification accuracy exceeds a pre-defined threshold, i.e., are predictive to some reasonable degree. Even with this filtering of "mini-classifiers" we end up with many thousands of "mini-classifier" candidates with performance spanning the whole range from borderline to decent to excellent performance.

The method continues with step e) of generating a master classifier (MC) by combining the filtered mini-classifiers using a regularized combination method. In one embodiment, this regularized combination method takes the form of repeatedly conducting a logistic training of the filtered set of mini-classifiers to the class labels for the samples. This is done by randomly selecting a small fraction of the filtered mini-classifiers as a result of carrying out an extreme dropout from the filtered set of mini-classifiers (a technique referred to as drop-out regularization herein), and conducting logistical training on such selected mini-classifiers. While similar in spirit to standard classifier combination methods (see e.g. S. Tulyakov et al., Review of Classifier Combination Methods, Studies in Computational Intelligence, Volume 90, 2008, pp. 361-386), we have the particular problem that some "mini-classifiers" could be artificially perfect just by random chance, and hence would dominate the combinations. To avoid this overfitting to particular dominating "mini-classifiers", we generate many logistic training steps by randomly selecting only a small fraction of the "mini-classifiers" for each of these logistic training steps. This is a regularization of the problem in the spirit of dropout as used in deep learning theory. In this case, where we have many mini-classifiers and a small training set we use extreme dropout, where in excess of 99% of filtered mini-classifiers are dropped out in each iteration.

In more detail, the result of each mini-classifier is one of two values, either "Early" or "Late" in this example. We can then use logistic regression to combine the results of the mini-classifiers in the spirit of a logistic regression by defining the probability of obtaining an "Early" label via standard logistic regression (see e.g. http://en.wikipedia.org/wiki/Logistic_regression)

$$P(\text{"Early"} | \text{feature for a spectrum}) = \frac{\exp\left(\sum_{mini\ classifiers} w_{mc} I(mc(\text{feature values}))\right)}{\text{Normalization}} \quad \text{Eq. (1)}$$

where I(mc(feature values))=1, if the mini-classifier mc applied to the feature values of a sample returns "Early", and 0 if the mini-classifier returns "Late". The weights $w_{rec}$ for the mini-classifiers are unknown and need to be determined from a regression fit of the above formula for all samples in the training set using +1 for the left hand side of the formula for the Late-labeled samples in the training set, and 0 for the Early-labeled samples, respectively. As we have many more mini-classifiers, and therefore weights, than samples, typically thousands of mini-classifiers and only tens of samples, such a fit will always lead to nearly perfect classification, and can easily be dominated by a mini-classifier that, possibly by random chance, fits the particular problem very well. We do not want our final test to be dominated by a single special mini-classifier which only performs well on this particular set and is unable to generalize well. Hence we designed a method to regularize such behavior: Instead of one overall regression to fit all the weights for all mini-classifiers to the training data at the same, we use only a few of the mini-classifiers for a regression, but repeat this process many times in generating the master classifier. For example we randomly pick three of the mini-classifiers, perform a regression for their three weights, pick another set of three mini-classifiers, and determine their weights, and repeat this process many times, generating many random picks, i.e. realizations of three mini-classifiers. The final weights defining the master classifier are then the averages of the weights over all such realizations. The number of realizations should be large enough that each mini-classifier is very likely to be picked at least once during the entire process. This approach is similar in spirit to "drop-out" regularization, a method used in the deep learning community to add noise to neural network training to avoid being trapped in local minima of the objective function.

Other methods for performing the regularized combination method in step (e) that could be used include:
Logistic regression with a penalty function like ridge regression (based on Tikhonov regularization, Tikhonov, Andrey Nikolayevich (1943). "Об устойчивости обратных задач" [On the stability of inverse problems]. Doklady Akademii Nauk SSSR 39 (5): 195-198.)

The Lasso method (Tibshirani, R. (1996). Regression shrinkage and selection via the lasso. J. Royal. Statist. Soc B., Vol. 58, No. 1, pages 267-288).

Neural networks regularized by drop-out (Nitish Shrivastava, "Improving Neural Networks with Dropout", Master's Thesis, Graduate Department of Computer Science, University of Toronto), available from the website of the University of Toronto Computer Science department.

General regularized neural networks (Girosi F. et al. Neural Computation, (7), 219 (1995)).

The above-cited publications are incorporated by reference herein. Our approach of using drop-out regularization has shown promise in avoiding over-fitting, and increasing the likelihood of generating generalizable tests, i.e. tests that can be validated in independent sample sets. The performance of the master classifier is then evaluated by how well it classifies the subset of samples forming the test set.

In step f), steps c)-e) are repeated in the programmed computer for different realizations of the separation of the set of samples into test and training sets, thereby generating a plurality of master classifiers, one for each realization of the separation of the set of samples into training and test sets. The performance of the classifier is evaluated for all the realizations of the separation of the development set of samples into training and test sets. If there are some samples which persistently misclassify when in the test set, the process optionally loops back and steps b), c) d), e) and f) are repeated with flipped class labels for such misclassified samples.

The method continues with step g) of defining a final classifier from one or a combination of more than one of the plurality of master classifiers. As an example, the final classifier is defined as a majority vote of all the master classifiers resulting from each separation of the development sample set into training and test sets, or alternatively by an average probability cutoff Bagged Feature Deselection or Filtering (Step 52, FIG. 2A, FIG. 5A)

The bagged feature deselection or filtering approach used above in step b) to create the reduced feature space from the original feature space evaluated in step a) will now be explained in more detail.

Referring now to FIG. 3, as inputs to the bagged filtering process 52 we have the development sample set data obtained as described in FIG. 2. Each of the N samples is assigned a class label, e.g., by a human operator after consideration of clinical or outcome data for the patient associated with the sample, or from observation of misclassification from a classifier as in step f) above. The class label can be such as "cancer", "no cancer", "benefit" (i.e., benefitted from a particular drug), "non-benefit", "early" (early relapse after commencement of treatment), "late" or otherwise, the particular choice of a moniker for the class label not being important. The "feature space" 50 consists of the set of y features in the measurement data, see FIG. 2. A third input to the process is the definition of a filter which is applied to classifier performance to test whether the particular feature, or set of features, used in each iteration of the flow chart of FIG. 3 met a standard or threshold of performance. The definition of the filter in step 120 is described below. As shown at block 122, the definition of the filter may possibly make use of other sample subsets or measurements, and if so in block 124 these other sample subsets or measurements are obtained so that they can be used with the filter, defined at step 120, in step 106.

Referring still to FIG. 3, at step 102 we generate a split of the development set of available samples (11 FIG. 2) into two subsets. See FIG. 4. One of the subsets is used for feature selection and deselection and classifier training (FIG. 4), and the remainder is left aside. If the problem has known confounding variables or there are particular characteristics that need to be taken into consideration, the split into two subsets can be done in a stratified manner. For example, suppose there is a known prognostic factor, such as performance status for lung cancer. It would be good to make sure that all the subsets contain representative proportions of patients in each performance status category. In this way, the final choice of (de)selected features, and any test or classifier built from it, will be well-tuned to the relative proportions of performance status categories expected in the target population. This is of additional importance when there is a factor that can act as a confounder for the clinical test to be created. If one were constructing a prognostic classifier for lung cancer that would add information to existing prognostic factors, and some realizations had random, strong imbalances between classes in performance status, the feature filtering for these realizations would tend to select features associated and correlated with performance status instead of features that are indicative of prognosis independent of performance status. So, some of the realizations would produce suboptimal sets of filtered features and the final choice of selected or deselected features could be correspondingly suboptimal. As shown by the loop 150, this splitting of the development set of samples into two subsets is performed many times, resulting in many different realizations of the separation of the development set of samples into training and remainder subsets.

One example of the separation of the development set of samples into two subsets is illustrated in FIG. 4, showing a first realization 102A, a second realization 102B, etc. up to realization M, 102M. M may for example be 100, 200 or more, depending on the number N of samples in the development sample set, and is typically greater than N. In the first iteration of the loop 150, realization 1 (102A) is created in which the set of N samples $S_1, S_2, S_3, \ldots S_N$ is separated into a training subset 200 consisting of the odd-numbered samples $S_1, S_3, S_5 \ldots$ and the remaining even numbered samples are set aside. The second iteration through the loop 150 results in a different realization 102B of the separation, in this example the training sub-set consists of samples $S_1, S_2, S_5, S_6 \ldots$ while the remainder subset consists of samples $S_3, S_4, S_7, S_8, \ldots$ The subsequent iterations result in realizations 3, 4, . . . M for M different iterations through the loop 150, as shown in FIG. 4. The aim is to explore the possible variety of subset realizations that can be drawn from the development sample set, so that it is possible to robustly select features over the whole ensemble and avoid overfitting the selected or deselected features to peculiarities of a particular sample set realization. Hence, the precise manner or algorithm by which the realizations are defined is not particularly important. However, in one possible embodiment a stratification of the samples may be performed in the generation of the realizations.

At step 104, a classifier is defined. This step can be simply defining the parameters for a KNN classification algorithm, such as values for k, identification of the realization of the training subset to be used as a reference set, and the identification of one or more features or sets of features in feature space to be used for the KNN classification algorithm. It will be noted in FIG. 2 that the feature space 50 can be composed of a large number of features, potentially in the hundreds or even thousands. In the process of FIG. 3, a step 114 is performed in which a list of all possible feature subsets of the features in the feature space is generated. This could be just a list of individual features, or a list of the individual features plus all possible pairs of features, or all possible sets of n different features wherein n<y (e.g., some integer such as 2, 3 or 5), or otherwise. At step 116 in the first iteration, one of the feature subsets is selected. For purposes of example, the first feature $f_1$ in the spectrum of FIG. 2 is selected and the classifier definition step 104 identifies or flags feature $f_1$ to use in the classification algorithm.

It will be noted that the present discussion and the following examples use simple k-nearest neighbor (KNN) classifiers. However, the type of classifier used is not important, and any type of classifier that can be trained on the single feature using the given subset of sample data can be used.

At step 106, the classifier defined at step 104 is applied to the training subset (200 in FIG. 4), and possibly also to other sets of samples where the class labels are known (124 in FIG. 3), and the classifier performance is assessed. The performance of the classifier can be evaluated in terms of accuracy (sensitivity and/or specificity) or in terms of any other metric that can be defined using the available clinical data for the samples. For example, if the aim is to identify patients likely to have good or poor survival on a particular treatment regimen as in the example of prognosis of patients with ovarian cancer treated with platinum doublet chemotherapy, the performance of the classifier could be assessed in terms of the hazard ratio (HR) between the resulting classification groups or the difference in medians of the resulting classification groups.

At step 108, a filter (defined at step 120) is applied to these performance estimates generated at step 106, such that the feature selected at step 116 only passes filtering if the classifier using this sample subset for training has adequate performance. The filter may be simple, such as demanding a minimal level of classification accuracy on the given training subset of samples, or may be compound, composed of any logical combination of criteria. As an example of a compound filter, if a classifier is required that is predictive of differential survival between two treatments, the filter could be a logical AND between a hazard ratio (HR) between the two classes in one treatment group that has to be smaller than a set threshold, e.g. 0.5, and a HR between the two classes in the other treatment group that has to be close to 1.0, e.g., greater than 0.75 and less than 1.33. The possibility of creating compound filters allows for the tuning of feature selection to the precise clinical question to be addressed, and this is the main advantage of this method over previously used approaches to feature selection and deselection. If there is a known confounder in a particular sample set, use of a compound filter can help eliminate confounding effects on feature selection and deselection. For example, if a classifier is to differentiate patients with cancer from patients without cancer, but the sample set available for training is plagued by a confounding variable, such that the cancer patients available for study have better liver function than the no cancer patients, standard methods may select features which differentiate between the patient samples according to liver function rather than to presence of cancer. With this new method, a compound filter can be implemented that demands that the feature produces a classifier with a minimal level of accuracy on the training samples and simultaneously classifies a separate set of patients with good liver function and without cancer as having no cancer, not as having cancer. Thus, a compound filter defined in this step can include a criterion of classification performance on a separate sample set, in this example a set of samples from patients with good liver function and no cancer.

At step 110, a "filtered feature list" (essentially just a list of the features f or feature subsets that pass filtering) is created based on the results of applying the filter step 108. In the first iteration of the loop 150, if the feature ($f_1$) selected at 116 meets the filtering criteria applied at step 108, it is added to the filtered feature list, otherwise it is not added. At step 112, for the given realization of the separation of the development set, a check is made to see if the last of the P feature subsets has been reached, and if not the process loops back as shown at 152 and another feature subset (such as the second feature $f_2$ in the list of features) is selected at step 116 and the steps 104, 106, 108, 110 and 112 are repeated. The process continues until the last feature(s) defined at step 114 is reached. At this point, the process proceeds to step 130 and a check is made to see if the required number of sample subset realizations (see FIG. 4) has been reached, and if not, the process loops back as indicated by 150 to step 102 and another sample subset realization is generated, such as realization #2 102B in FIG. 4.

The process proceeds into a second iteration of the loop 150, in which steps 102, 104, 116, 106, 108, 110 and 112 are performed. This next iteration results in possible inclusion of the feature(s) used in the iterations to the filtered feature list created at step 110.

At step 132, after all the required sample subset realizations (102M, FIG. 4) have been subject to the process of FIG. 3 the filtered feature list is then analyzed. In particular, a sum is performed of the number of times each feature subset (single features), ordered pairs of features, or possibly triplets of features, etc.) appears in the filtered feature list. This summing can be performed using weights if a weighted ensemble sum is required. The sums generated at step 132 can then be used to select, or deselect features, when generating or defining a final classifier from the development sample set.

In the present example, using the process of FIGS. 3 and 4 within each iteration of loop 346 of FIG. 5B we reduced an initial set of 350 features down to a reduced feature set of approximately 60 features (see Table 18 for the features used in the classifiers of this disclosure which represent the final iteration of loop 346 when few or no samples misclassify at 344 of FIG. 5B). Further details on the bagged filtering process of FIGS. 3 and 4 can be found in U.S. patent application Ser. No. 15/091,417 filed Apr. 5, 2016, the contents of which are incorporated by reference herein. The details are not particularly important and are omitted for the sake of brevity.

Turning now to FIG. 5A, the classifier development process will be described in further detail in the context of the ovarian/platinum chemotherapy classifier.

The subset of 129 patients with available DFS data and DFS known to be in excess of 1 month were selected from the whole cohort of 138 patients. This subset was then split in half stratified on outcome and taking account of how features were related to outcome within each half, as explained in Appendix B of our prior provisional application, to produce a matched development and internal validation set. The resulting development set of 65 samples was used to develop and initial or first level classifier, referred to as Classifier A, in the following discussion. It will be appreciated that it would also be possible to develop a classifier from the whole cohort, e.g., where there is another cohort of samples available for a validation exercise.

In particular, in order to arrive at this split the following steps were taken:

All samples are ordered by DFS censoring and DFS time.

Each sample is given a name in the definition column either "Group1" or "Group2". Starting with "Group1" the next sample will get "Group2" then third sample will get "Group1" and so forth. This will split the 129 samples into 65 "Group1" and 64 "Group2".

The labels from the definition column are then copied over to the groupname column. The stratified realization generator was run and 625 realizations were created. The stratified realization generator was run 32/33 on "Group1" and 32/32 on "Group2" with test group as "Validation".

Each realization was analyzed in terms of the fraction of features correlated with OS (analyses process described below). A realization that minimized the difference of such fraction of features across subsets was chosen.

The assignment of individual samples to development set and validation set is shown in Table 15 at the end of this specification.

Analysis of the Fraction of Features Correlated with OS

For each feature, the samples are ordered by feature values and divided in two groups, taking as threshold for separation between groups the expression value of the nth percentile (we used the 20th, 30th, 40th, 50th, 60th, 70th and 80th percentiles). A univariate Cox proportional analysis is then run (in Matlab-coxphfit function) taking the groups defined previously as the discriminatory variable with censored time-to-event data. As outputs, the univariate Cox proportional analysis provides the actual hazard ratio between groups and its significance in terms of a p-value. We then calculate the fraction of significant features, i.e. those with a p-value lower than 0.05.

The process described in the previous paragraph was performed on all 625 realizations and, after inspection of the results, realization 21 was picked as the best split between development split and validation split. The fraction of features correlated with OS with a p-value lower than 0.05 as function of the considered percentile is shown in a figure in Appendix B of our prior provisional application for the chosen subset. In addition and for completeness the fraction of features correlated with DFS with the same level of confidence (as given by the p-value) is also shown in that figure.

At step 302, a definition of the two class labels (or groups) for the samples in the development set 300 was performed. While some preliminary approaches used for classifier development employed well-defined class labels, such as response categories or chemo-resistance (yes/no), these proved to be unsuccessful. All approaches discussed in this report make use of time-to-event data for classifier training. In this situation class labels are not obvious and, as shown in FIGS. 5A and 5B, the methodology uses an iterative method to refine class labels (loop 346) at the same time as creating the classifier. At step 302, an initial guess is made for the class labels. Typically the samples are sorted on either DFS or OS and half of the samples with the lowest time-to-event outcome are assigned the "Early" class label (early death or progression, i.e. poor outcome) while the other half are assigned the "Late" class label (late death or progression, i.e. good outcome). Classifiers (step 330) are then constructed using the outcome data and these class labels for many different training sets (312) drawn from the development set and the associated test sets (310) classified. The class labels of samples which persistently misclassify when in the test set across the multiple training/test set splits (loop 335) are flipped (344 and loop 346) and the resulting new set of class labels are then used for a second iteration of the classifier construction step. This process is iterated until convergence. The Early and Late groups are shown at 304 and 306.

At step 308, the Early and Late samples of the development set (300) are then divided randomly into training (312) and test sets (310). The training set (312) is then subject to steps 320, 326 and 330. In step 320, many k-nearest neighbor (KNN) mini-classifiers (mCs) that use the training set as their reference set are constructed (defined) using subsets of features from the reduced set of spectral features identified. For these investigations, all possible single features and pairs of features were examined (s=2); however, one could choose to explore the reduced feature space more deeply using triplets (s=3) or even higher order combinations of features. All approaches described in this document all use k=9, but other values of k such as 7 or 11 could be considered.

In step 326 a filtering process was used to select only those mini-classifiers (mC) that had useful or good performance characteristics. This can be understood in FIG. 5A by the spectra 324 containing many individual features (shown by the hatched regions) and the features alone and in pairs are indicated in the reduced feature space 322. For some of the KNN mini-classifiers, the features (singly or in pairs) perform well for classification of the samples and such mini-classifiers are retained (indicated by the "+" sign in FIG. 5 at 328) whereas others indicated by the "−" sign are not retained.

To target a final classifier that has certain performance characteristics, these mCs were filtered as follows. Each mC is applied to its training set and performance metrics are calculated from the resulting classifications of the training set. Only mCs that satisfy thresholds on these performance metrics pass filtering to be used further in the process. The mCs that fail filtering are discarded. For this project hazard ratio filtering was used. For hazard ratio filtering, the classifier was applied to the training set. The hazard ratio for OS was then calculated between the group classified as Early and the rest classified as Late. The hazard ratio had to lie within specified bounds for the mC to pass filtering.

At step 330, we generated a master classifier (MC) for each realization of the separation of the development set into training and test sets at step 308. Once the filtering of the mCs was complete, at step 332 the mCs were combined in one master classifier (MC) using a logistic regression trained using the training set class labels, step 332. To help avoid overfitting the regression is regularized using extreme drop out with only a small number of the mCs chosen randomly for inclusion in each of the logistic regression iterations. The number of dropout iterations was selected based on the typical number of mCs passing filtering to ensure that each mC was likely to be included within the drop out process multiple times. All approaches outlined in this document left in 10 randomly selected mCs per drop out iteration and used 10,000 drop out iterations.

At step 334, we evaluated the performance of the MC arrived at in step 332 and its ability to classify the test set of samples (310). With each iteration of step 320, 326, 330, 334 via loop 335 we evaluate the performance of the resulting MC on its ability to classify the members of the test set 310. In particular, after the evaluation step 334, the process looped back via loop 335 to step 308 and the generation of a different realization of the separation of the development set into training and test sets. The process of steps 308, 320, 326, 330, 332, 334 and looping back at 335 to a new separation of the development set into training and test sets (step 308) was performed many times. The use of multiple training/test splits avoids selection of a single, particularly advantageous or difficult, training set for classifier creation and avoids bias in performance assessment from testing on a test set that could be especially easy or difficult to classify.

At step 336, there is an optional procedure of analyzing the data from the training and test splits, and as shown by block 338 obtaining the performance characteristics of the MCs from each training/test set split and their classification results. Optional steps 336 and 338 were not performed in this project.

At step 344, we determine if there are samples which are persistently misclassified when they are present in the test set 310 during the many iterations of loop 335. If so, we flip the class label of such misclassified samples and loop back in step 346 to the beginning of the process at step 302 and repeat the methodology shown in FIGS. 5A and 5B.

If at step 344 we do not have samples that persistently misclassify, we then proceed to step 350 and define a final classifier in one of several ways, including (i) a majority vote of each master classifier (MC) for each of the realizations of the separation of the development set into training and test sets, or (ii) an average probability cutoff.

The output of the logistic regression (332) that defines each MC is a probability of being in one of the two training classes (Early or Late). These MC probabilities can be averaged to yield one average probability for a sample. When working with the development set 300, this approach is adjusted to average over MCs for which a given sample is not included in the training set ("out-of-bag" estimate). These average probabilities can be converted into a binary classification by applying a threshold (cutoff). During the iterative classifier construction and label refinement process, classifications were assigned by majority vote of the individual MC labels obtained with a cutoff of 0.5. This process was modified to incorporate only MCs where the sample was not in the training set for samples in the development set (modified, or "out-of-bag" majority vote). This procedure gives very similar classifications to using a cutoff of 0.5 on the average probabilities across MCs.

After the final classifier is defined at step 350, the process optionally continues with a validation step 352 in which the master classifier defined at step 350 is tested on an internal validation set of samples, if it is available. In the present example, the initial set of samples was divided into a development set (300) and a separate internal validation set, and so this validation set existed and was subject to the validation step 352. See FIGS. 6 and 7. Ideally, in step 354 this master classifier as defined at step 350 is also validated on an independent sample set.

Classifier A Development

Figure 6A:
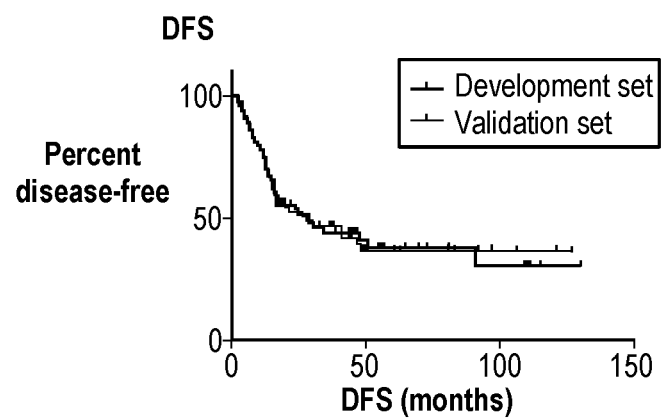
FIGS. 6A and 6B are Kaplan-Meier plots of time to event data for the 129 patients in the development sample set with available clinical data. DFS>1 month, and mass spectral data from pretreatment samples, showing the plots for a split of the sample set into development (N=65) and validation (N=64) sets.
Figure 6B:
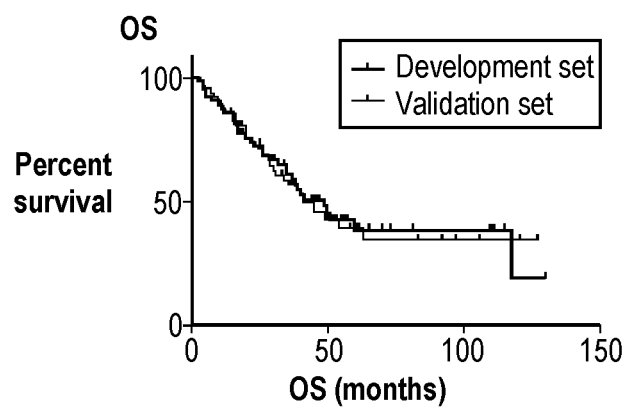
Figure 7A:
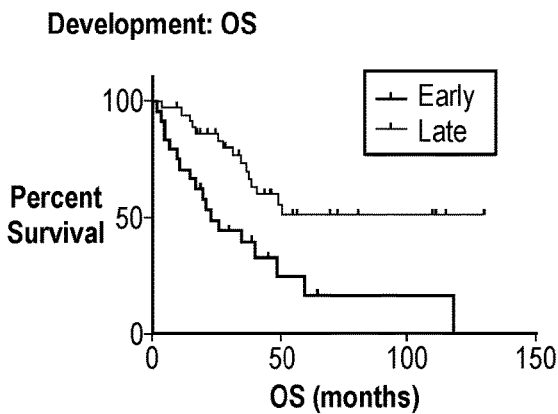
FIGS. 7A-7D are Kaplan-Meier plots of OS and DFS by Early and Late classification groups produced by the first tier or "Classifier A" classifier, for the 129 patients split into development and validation sets.
Figure 7B:
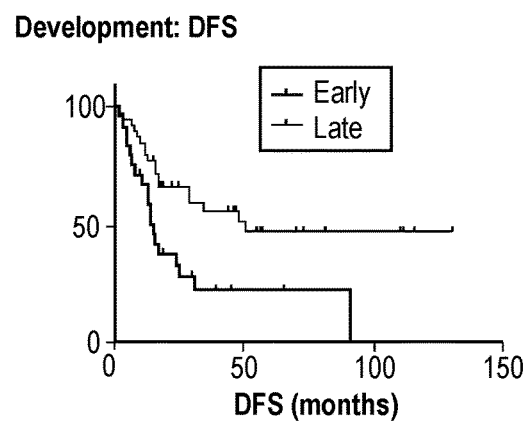
Figure 7C:
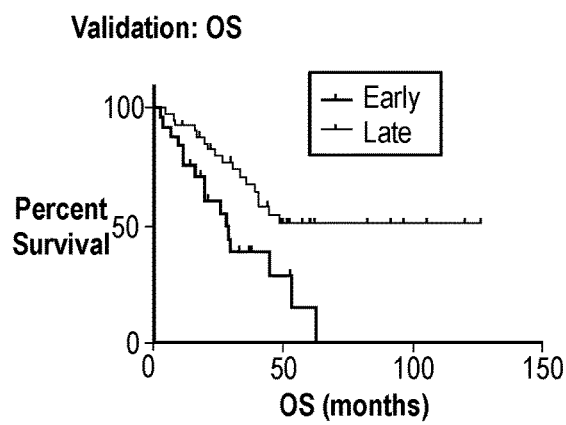
Figure 7D:
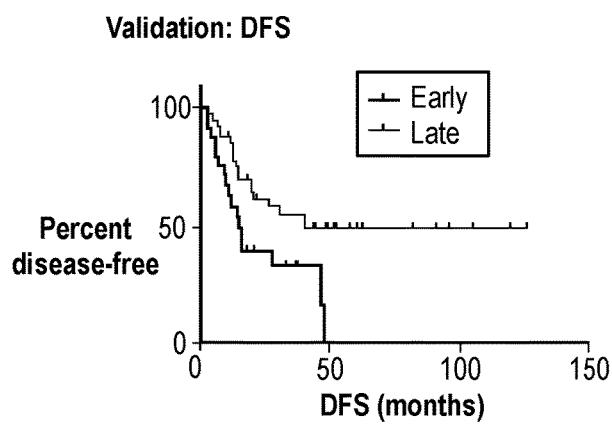

Initial new classifier development was performed using the process of FIGS. 5A and 5B described in detail above, using 129 samples. This was a reduced set including only patients with DFS greater than 1 month. The sample number allowed for a split into a development set and an internal validation set for classifier development. The split into development and validation sets was stratified by censoring of DFS and OS. The assignment of individual samples to validation or development sets is shown and described in detail in appendix A and appendix B, respectively. The development set had 65 patients and validation set had 64 patients. The clinical characteristics are listed for the development and validation split in table 2. Comparison of the time-to-event data between development and validation sets is shown in FIGS. 6A and 6B.

TABLE 2

Baseline characteristics of patients with available spectra split into development (n = 65) and internal validation (n = 64) sets

| | | Development set n(%) | Validation set n(%) |
|---|---|---|---|
| Histology | serous | 47 (72) | 47 (73) |
| | non-serous | 18 (28) | 17 (27) |
| VeriStrat Label | Good | 50 (77) | 53 (83) |
| | Poor | 15 (23) | 11 (17) |
| FIGO | NA | 16 (25) | 21 (33) |
| | 1 | 6 (9) | 7 (11) |
| | 2 | 1 (2) | 2 (3) |
| | 3 | 30 (46) | 21 (33) |
| | 4 | 12 (18) | 13 (20) |
| Histologic Grade | NA | 1 (2) | 1 (2) |
| | 1 | 2 (3) | 5 (8) |
| | 2 | 25 (38) | 23 (36) |
| | 3 | 37 (57) | 35 (55) |
| Metastatic Disease | yes | 9 (14) | 7 (11) |
| | no | 56 (86) | 57 (89) |
| Residual Tumor | yes | 27 (42) | 20 (31) |
| | no | 38 (58) | 44 (69) |
| Age | Median (range) | 57 (18-88) | 59 (20-83) |

This development set of samples was used with its associated clinical data in the procedure of FIGS. 5A and 5B, as described above, to generate a classifier (Classifier A) able to stratify patients into two groups with better ("Late"=late progression) and worse ("Early"=early progression) outcomes. The features used in Classifier A (the reduced feature space created by feature deselection in the final iteration of loop 346 FIG. 5) are listed in Table 18. Performance of the classifier was assessed within the development set using out-of-bag estimates as previously described. The classifier was then applied to the validation set to assess its performance in an internal validation set not used at all in the development of the classifier (352 in FIG. 5B).

Performance of Classifier A

The performance of the Classifier A was assessed using Kaplan-Mieier plots of DFS and OS between samples classified as Early and Late, together with corresponding hazard ratios (HRs) and log-rank p values. The results are summarized in tables 3 and 4.

TABLE 3

Performance summary for Classifier A

| | #Early/#Late | OS HR (95% CI) | OS log-rank p | OS Median (Early, Late) | DFS HR (95% CI) | DFS log-rank p | DFSMedian (Early, Late) |
|---|---|---|---|---|---|---|---|
| Development | 25/40 | 2.76 (1.54-6.82) | 0.002 | 23, not reached (Months) | 2.44 (1.42-5.77) | 0.004 | 15, 51 (Months) |

TABLE 3-continued

Performance summary for Classifier A

| | #Early/#Late | OS HR (95% CI) | OS log-rank p | OS Median (Early, Late) | DFS HR (95% CI) | DFS log-rank p | DFSMedian (Early, Late) |
|---|---|---|---|---|---|---|---|
| Validation | 24/40 | 2.54 (1.44-6.67) | 0.005 | 28, not reached (Months) | 2.31 (1.33-5.69) | 0.008 | 15, 41 (Months) |

TABLE 4

Performance summary for classifier run on all the 138* samples

| | #Early/#Late | OS HR (95% CI) | OS log-rank p | OS Median (Early, Late) | DFS HR (95% CI) | DFS log-rank p | DFS Median (Early, Late) |
|---|---|---|---|---|---|---|---|
| Whole set | 54/84 | 2.65 (1.89-5.21) | <0.001 | 26, not reached (Months) | 2.44 (1.80-4.72) | <0.001 | 14, 48 (Months) |

*Note:
2 samples of the 138 samples did not have DFS time-to-event data.

Figure 8A:
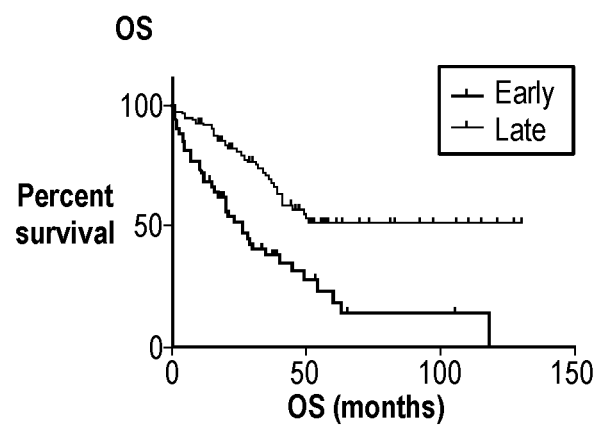
FIGS. 8A and 8B are Kaplan-Meier plots of OS and DFS by Early and Late classification groups, for the "Classifier A" run on all 138 samples.
Figure 8B:
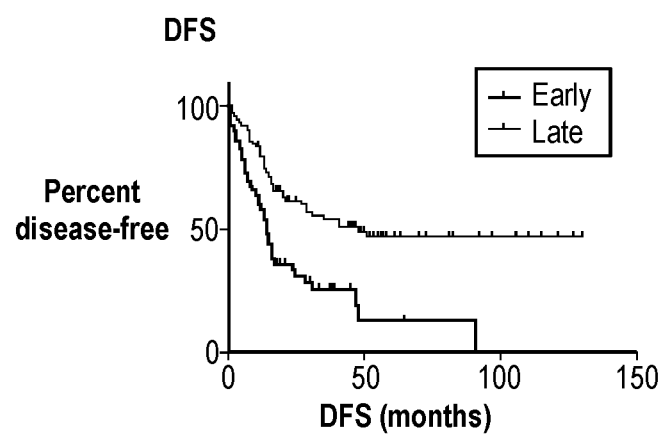

Kaplan-Meier plots corresponding to the data in table 3 are shown in FIGS. 7A-7D and data in table 4 are shown in FIGS. 8A and 8B. The classifications per sample are listed in Table 16 at the end of this specification.

Of note for prediction of chemo-resistance: DFS is 74% at 6 months in the Early group, compared with 93% in the Late group and at 12 months DFS is 58% in the Early group compared with 80% in the Late group. Of 14 patients with DFS of months or less 9 (64%) are classified as Early and of the 20 patients with DFS of 6 months or less 14 (70%) are classified as Early, see table 5.

TABLE 5

DFS before 4 months, 6 months, 10 and 12 months

| | Early | Late | P value |
|---|---|---|---|
| DFS ≤ 4 months | 9 | 5 | 0.079 |
| No DFS ≤ 4 months | 44 | 77 | |
| DFS ≤ 6 months | 14 | 6 | 0.005 |
| No DFS ≤ 6 months | 39 | 76 | |
| DFS ≤ 10 months | 19 | 13 | 0.007 |
| No DFS ≤ 10 months | 32 | 68 | |
| DFS ≤ 12 months | 22 | 16 | 0.006 |
| No DFS ≤ 12 months | 29 | 63 | |

Baseline clinical characteristics are summarized by classification group in table 6.

TABLE 6

Clinical characteristic by classification group when run on 138 samples

| | | Early set (N = 54) n (%) | Late set (N = 84) n (%) | P value |
|---|---|---|---|---|
| Histology | serous | 45 (83) | 55 (65) | 0.031 |
| | non-serous | 9 (17) | 29 (35) | |
| VeriStrat Label | Good | 27 (50) | 83 (99) | <0.001 |
| | Poor | 26 (48) | 1 (1) | |
| | Indeterminate | 1 (2) | 0 (0) | |
| FIGO | 1 | 0 (0) | 13 (15) | <0.001† |
| | 2 | 1 (2) | 2 (2) | |
| | 3 | 21 (39) | 33 (39) | |
| | 4 | 20 (37) | 9 (11) | |
| | NA | 12 (22) | 27 (32) | |

TABLE 6-continued

Clinical characteristic by classification group when run on 138 samples

| | | Early set (N = 54) n (%) | Late set (N = 84) n (%) | P value |
|---|---|---|---|---|
| Histologic Grade | NA | 0 (0) | 2 (2) | 0.379* |
| | 1 | 1 (2) | 6 (7) | |
| | 2 | 20 (37) | 33 (39) | |
| | 3 | 33 (61) | 43 (51) | |
| Metastatic Disease | yes | 14 (26) | 6 (7) | 0.003 |
| | no | 40 (74) | 78 (93) | |
| Residual Tumor | yes | 38 (70) | 15 (18) | <0.001 |
| | no | 16 (30) | 69 (82) | |
| Age | Median (range) | 60 (35-88) | 57.5 (18-83) | |

*1 + 2 vs 3, †1-3 vs 4

Test classification is significantly associated with histology, FIGO score and presence of metastatic disease. Table 7 shows the results of multivariate analysis of OS and DFS for the whole cohort.

TABLE 7

Multivariate analysis of the whole cohort

| | OS | | DFS | |
|---|---|---|---|---|
| Covariate | HR (95% CI) | P value | HR (95% CI) | P value |
| Early vs Late | 1.68 (0.99-2.84) | 0.054 | 1.63 (0.97-2.72) | 0.064 |
| FIGO 1-3 vs 4 | 0.33 (0.18-0.59) | <0.001 | 0.46 (0.26-0.82) | 0.009 |
| FIGO NA vs 4 | 0.46 (0.24-0.87) | 0.018 | 0.67 (0.35-1.28) | 0.220 |
| Non-Serous vs Serous | 0.88 (0.47-1.64) | 0.681 | 0.86 (0.47-1.57) | 0.621 |
| Tumor Residual (yes vs no) | 2.40 (1.38-4.16) | 0.002 | 2.07 (1.23-3.49) | 0.006 |

Test classification retains a trend to significance as a predictor of OS and DFS when adjusted for known prognostic factors.

Second Classifier Development ("Classifier B")

While the performance of Classifier A was quite promising, we hoped to be able to improve performance. In particular we have been successful in isolating subgroups of patients who exhibit particularly poor outcomes by taking the subgroup of patients who are classified as Early by an initial classification and further stratifying within this population by using this subgroup to train a second, follow-up classifier. This approach was used to create Classifier B.

This classifier was developed using the samples that had been classified as "Early" from either the development set (n=25) or the validation set (n=24) by Classifier A, with the addition of the 9 samples from patients with exceptionally poor outcomes (DFS less than 2 months) that were not used in the development of Classifier A. This subset of samples with associated clinical data was used in the classifier development procedure of FIGS. 5A and 5B as explained above to create a new classifier, Classifier B, again assigning each sample in the reduced development set one of two classifications, "Early" or "Late". To avoid confusion with the Early and Late classification labels assigned by the Classifier A, we can refer to these labels as "Earlier" or "Later". The particular choice of moniker is not particularly important. What is important is that these Early, poor performing patients identified by Classifier A, are further stratified by Classifier B into two groups, one performing relatively better (Late or Later) and another group that performs particularly poorly (Early or Earlier). The features used in Classifier B (the reduced feature space created by feature deselection in the final iteration of loop 346 FIG. 5) are listed in Table 18. In particular, this classifier was able to split the patients in its development set into two groups with better and worse DFS and OS, as shown in the Kaplan-Meier plots of FIGS. 10A and 10B. Twenty eight of the 58 samples used in development were classified as Early. Note in FIG. 10B that those samples classified by Classifier B as Earlier have much poorer OS and DFS than those patients classified as Later.

Figure 9:
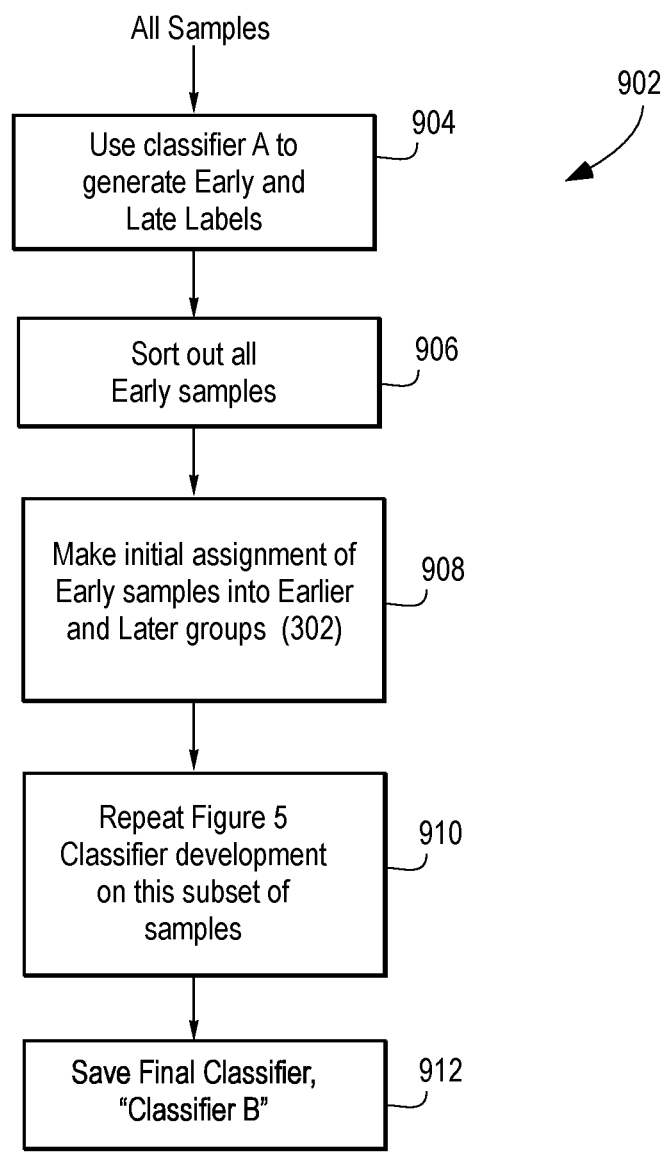
FIG. 9 is a flow chart showing a process for generating a second tier classifier ("Classifier B") from those development set samples that were classified as "Early" by the first tier "Classifier A" classifier.
Figure 10A:
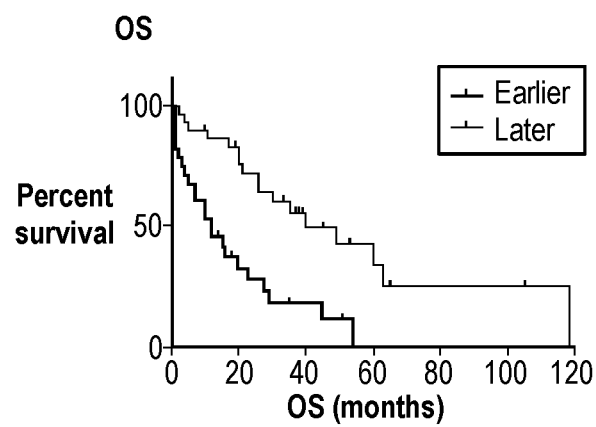
Figure 10B:
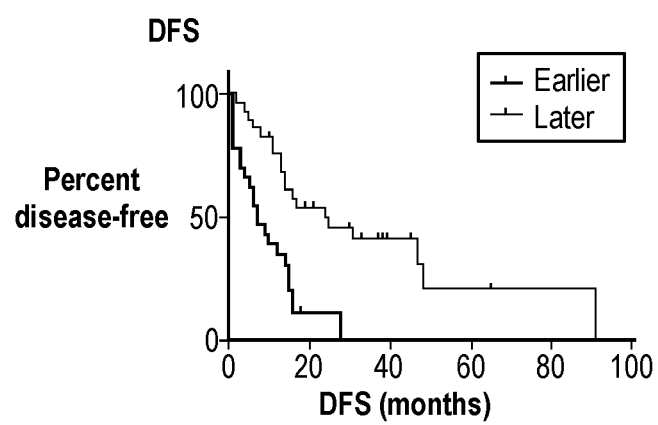

The procedure we used for generating Classifier B is illustrated in flow chart form in FIG. 9 as process 902. At step 904, we used Classifier A to generate Early or Late labels for all the samples in the entire development set. At step 906 we sorted out all the Early samples. At step 908 we made an initial label assignment of either Earlier or Later for this subset of samples based on DFS and OS data in performing step 302 of the classifier development process of FIG. 5. At step 910 we then repeated the classifier generation method of FIG. 5 on this subset of samples as the development set (augmented by 9 samples that we had decided not to use in development or validation sets for classifier A as their DFS was one month or less). The process generated a new final classifier (step 350), the parameters of which were saved at step 912. These parameters include the identification of the set of samples used for classifier development, the features passing filtering in the miniClassifiers, the logistic regression weights computed in step 332, the value of k in the miniClassifiers, and the definition of the final classifier at step 350.

Third Classifier Development "Classifier C"

We have been successful in isolating subgroups of patients who demonstrate particularly good outcomes by identifying clinically distinct subgroups of the patient cohort and developing a classifier, as described above in FIGS. 5A and 5B, for each distinct subgroup. We apply these multiple classifiers to a test sample and if the sample always classifies as "Late" with each of the multiple classifiers we assign an overall classification of "Good" to indicate a likelihood of a particularly good prognosis. This approach was used to create Classifier C (which is composed of the multiple classifiers C1, C2, C3, and C4).

Classifier C was created using all 138 available samples. Four different classifiers (C1, C2, C3, and C4) were generated using the same procedure of FIGS. 5A and 5B as was used for Classifier A and Classifier B, with development sets chosen to be clinically distinct subsets of the total cohort of 138 patients. Given the available clinical data, histology and presence/absence of residual tumor after surgery were chosen to determine the clinically distinct subsets.

Classifier C1 was developed on the subset of 60 patients with non-serous histology or serous histology together with unknown FIGO score.

Classifier C2 was developed on the subset of 78 patients not used to develop Classifier C1. These patients all had serous histology, and a known FIGO score.

Classifier C3 was developed on the subset of 53 patients with residual tumor after surgery.

Classifier C4 was developed on the subset of 85 patients with no residual tumor after surgery.

Note: when ovarian cancer is diagnosed it is staged (usually using FIGO score) and given a histological type and grade by a pathologist from tumor tissue taken at surgery (biopsy is generally avoided in ovarian cancer as it is better to remove the tumor(s) whole). The predominant histological subtype for ovarian cancer is serous. Other less common types include mucinous, endometriod, and clear cell. These last 3 are combined into the "non-serous" histology type. Non-serous histology compared with serous histology is a positive prognostic factor.

As the goal of Classifier C was to be able to identify ovarian cancer patients that would likely do particularly well on platinum chemotherapy, the selection of the clinical subgroups for individual generation of classifiers was done with the idea of selecting clinically different subgroups known to have different prognosis and seeing which patients always do well. In particularly, for a patient to perform really well, ideally you they should be classified as performing well in comparison with all possible clinically distinct population. Hence, it doesn't really matter how one selects the clinical subgroups, but they need to be clinically different and should ideally be clearly different in terms of patient prognosis. It would be possible in some situations that one could select clinical subgroups based on tumor size. Here, we looked at the clinical characteristics that we had available which we knew were prognostic factors (FIGO score, histology, residual tumor). We split the cohort into two for each of these factors, and made 2 classifiers, one on each subset. Then we looked to see whether the resulting classifications were very different depending on the two classifiers for each factor. It turned out that histology and residual tumor worked best and complemented each other and adding in the FIGO score based classifiers didn't change the classifier performance much. The original plan was to then make more subgroups using one or more of these factors. But, we discovered that just using the two classifiers for each of histology and residual tumor already worked very well, so we didn't pursue further clinical subgroups, but in theory it would certainly possible to do so. One might get the most advantage from this method by looking at the two most different subgroups e.g. all no residual tumor vs all residual tumor. Adding in further subgroups with admixtures of the two extreme groups, does not add so much in terms of principle refinement of the groups, but it does protect against the possibility of getting results in one of the two extreme subgroup classifiers that are just due to the particularities of the development set and not really due to the clinically different subsets. This is always a danger when, as usual, we have relative low numbers of patient samples to work with, and having more than two subgroups per clinical characteristic might help to avoid this.

All four classifiers were created to split samples into two classes, Early and Late. Each classifier was then applied to all 138 samples. Classifications of samples within the development set of each classifier were generated using out-of-bag estimates. This provided four classifications for each sample, one from each of the four classifiers, C1, C2, C3, and C4. Samples receiving a "Late" classification from all four classifiers were assigned a "Good" classification label.

The above method for generating Classifier C is illustrated in flow chart form in FIG. 11 as procedure 1102. At step 1102, one defines up to N clinically distinct subgroups of patients from the classifier development set, e.g., by inspection of the clinical data that is associated with each of the samples. The development set is then divided into subsets 1, 2, 3, . . . N, where N is typically an integer of 2 or more. At step 1108, we repeat the classifier development process (FIGS. 5A and 5B) for each of the subsets 1 . . . N. In the present ovarian context, N=4 and the subgroups are as identified above. At step 1110, the final classifier resulting at step 350 from procedure of FIGS. 5A and 5B is saved for each of the subsets, resulting in classifiers C1, C2, . . . CN. The features used in Classifiers C1, C2, C3, and C4 (the reduced feature space created by feature deselection in the final iteration of loop 346 FIG. 5 for each of the four classifiers) are listed in Table 18.

Figure 12:
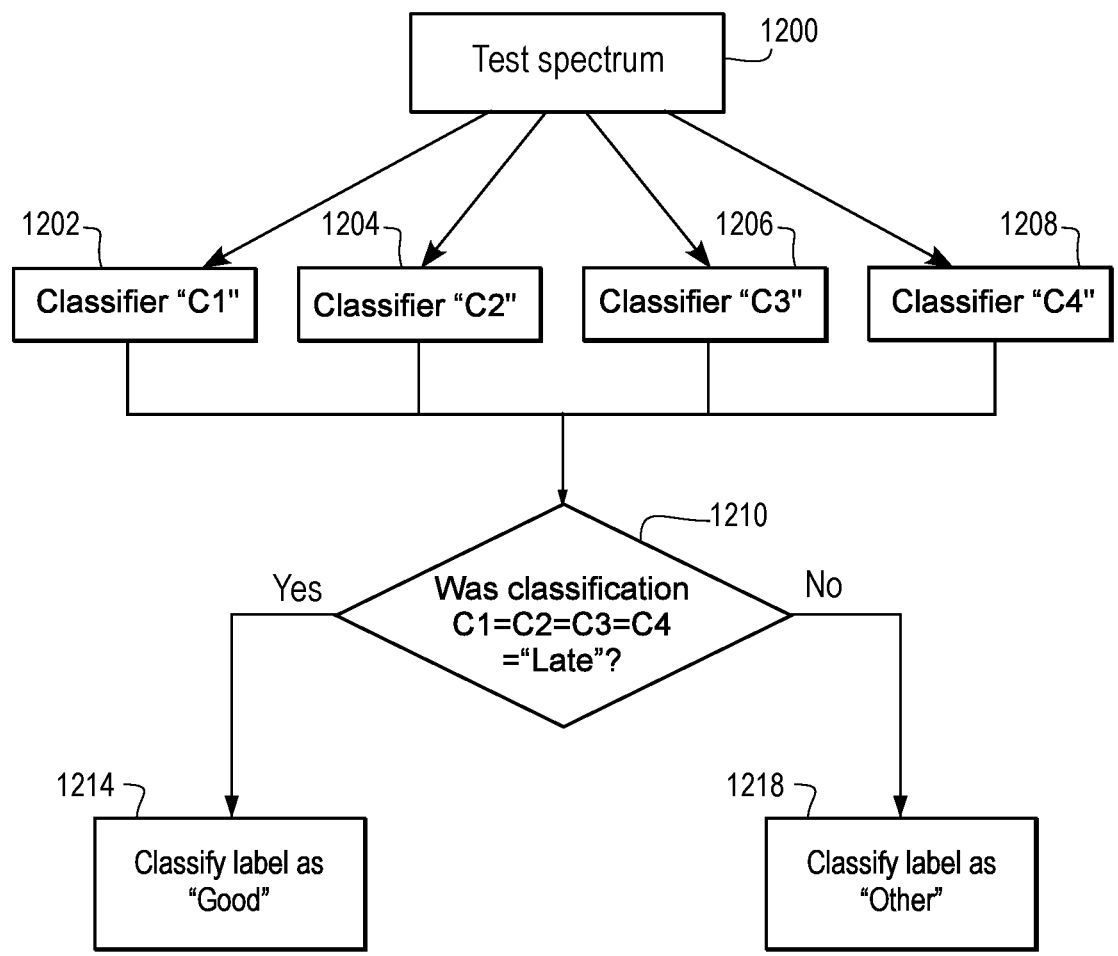
FIG. 12 is a diagram showing the construction of a third tier Classifier C, and how it could be used to generate a "Good' class label based on the results of classification by each of the members of the third tier.

The composition of Classifier C is shown in FIG. 12. A test spectrum 1200 (feature values for the features used for classification of a test sample) is supplied to each of the classifiers 1202, 1204, 1206 and 1208. Each classifier generates a label, either Early or Late in this example. At step 1210, a check is made to determine whether each classifier C1 . . . C4 produced the Late class label. If so, the class label Good is reported at step 1214. In the present context, this class label indicates that the ovarian cancer patient is predicted to have a particularly good outcome on platinum chemotherapy. Conversely, if at step 1210 the classifiers are not unanimous in producing the Late class label, the class label Other (or the equivalent) is reported at step 1218. It will be noted that the Classifier C of FIG. 12 (strictly speaking, the set of parameters stored in memory including reference set, logistic regression weights, identification of features for miniClassifiers, etc.) includes not only the underlying classifiers C1 . . . C4 defined per FIG. 5A but also the logic for comparing the results of each of the classifiers C1 . . . C4 and generating a final a class label depending on the results of the classifiers C1 . . . C4.

Hierarchical Combination of Classifiers

Classifiers A, B and C can be used in a hierarchical or ordered combination. For example, Classifier A can be used to initially classify a test sample, and if the Classifier A produces an Early class label then Classifier B is employed to generate a class label. If Classifier B produces an Early or Earlier label, the patient providing the samples is expected to perform particularly poorly on the platinum chemotherapy (platinum refractory or platinum resistant). If Classifier A produces the Late class label, the patient is predicted to perform well on platinum chemotherapy.

As another example, Classifier A and C can be used in combination. Classifier A can be used to initially classify a test sample, and if the Classifier A produces an Early class label the patient is predicted perform particularly poorly on the platinum chemotherapy (platinum refractory or platinum resistant). If Classifier A produces the Late class label, the patient sample is then subject to classification by Classifier C. If Classifier C produces a Late class the patient providing the samples is expected to perform very well on platinum chemotherapy and the Good class label is returned. If Classifier C produces an Early class label, the Other class label can be returned. The meaning and usage of the Other class label is explained below.

Figure 13:
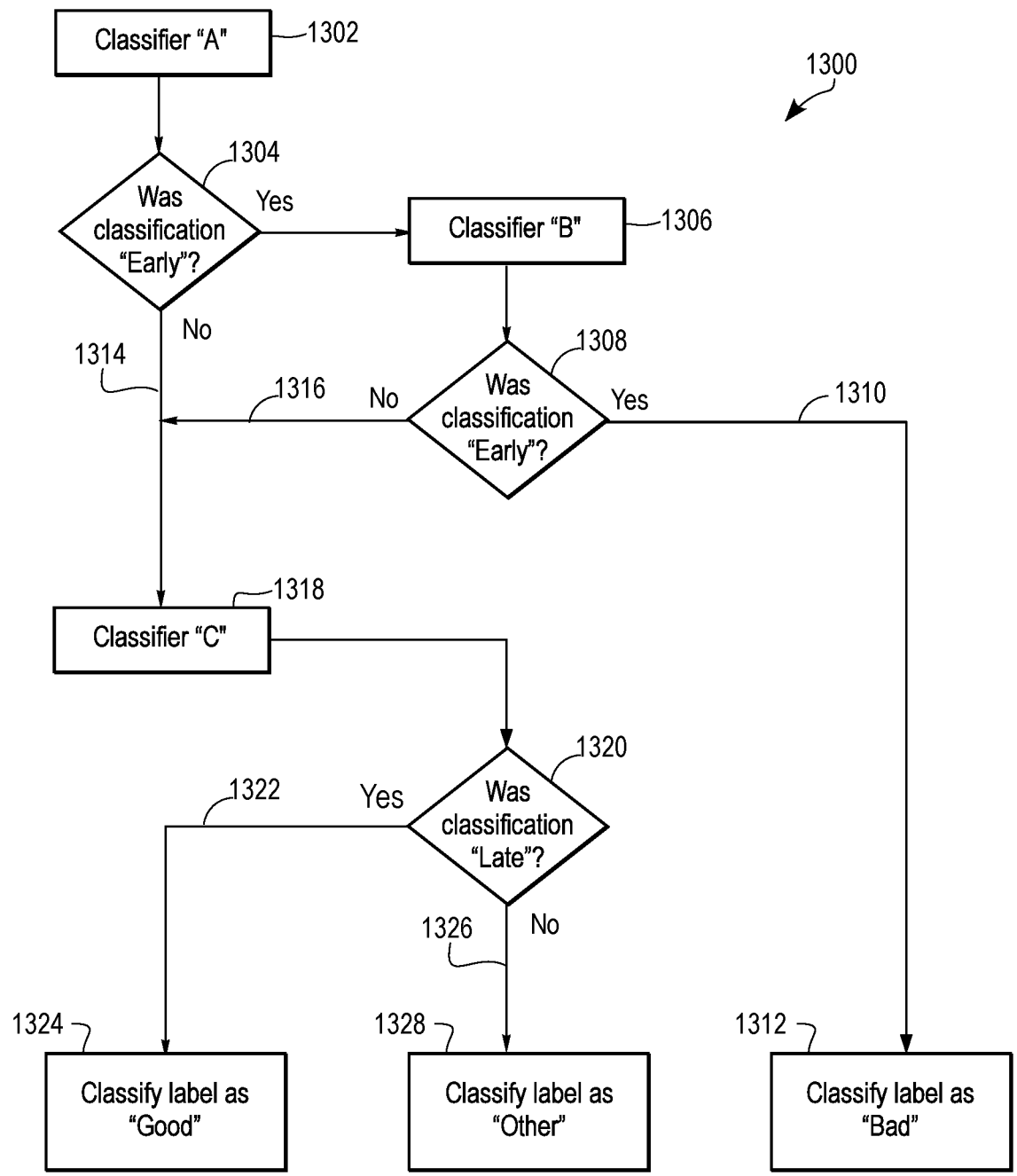
FIG. 13 is a diagram showing the construction of a final classifier composed of a three-stage hierarchical classifier.

Furthermore, Classifiers A, B and C can also be used in a hierarchical or ordered manner as shown in FIG. 13. A test sample is first classified by Classifier A, step 1302. If it classifies as Early (step 1304), it is then classified by Classifier B (1306). At step 1308 the class label produced by Classifier B is inspected. If Classifier B also returns an Early classification (branch 1310) an overall label of "Bad" is returned (poor prognosis, platinum refractory or platinum resistant). If Classifier B returns a Late classification (branch 1316) or Classifier A returns a Late classification (branch 1314) the sample is classified by Classifier C (1318). Classifier C is trained to identify patients performing particularly well on the therapy. At step 1320 a check is made of the classification label produced by Classifier C. If Classifier C returns a "Late" classification (branch 1322), an overall "Good" classification is assigned to the sample (1324). If Classifier C does not return a "Late" classification (branch 1326), the sample receives an overall "Other" classification (1328).

Figure 14:
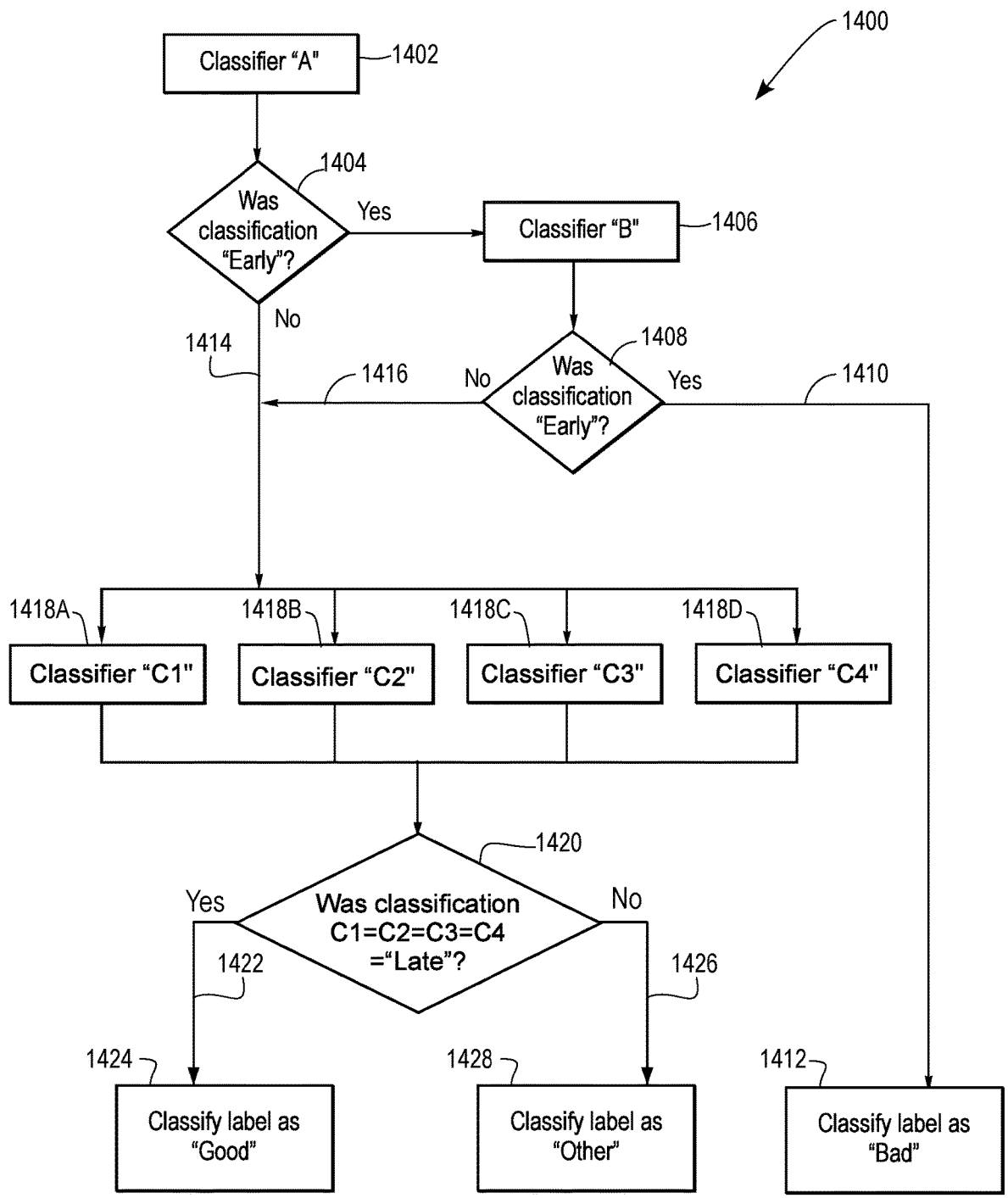
FIG. 14 is a diagram showing the construction of an alternative final classifier in which the third stage of the three-stage hierarchical classifiers is made up of four individual classifiers developed from clinically distinct subgroups.
Figure 15:
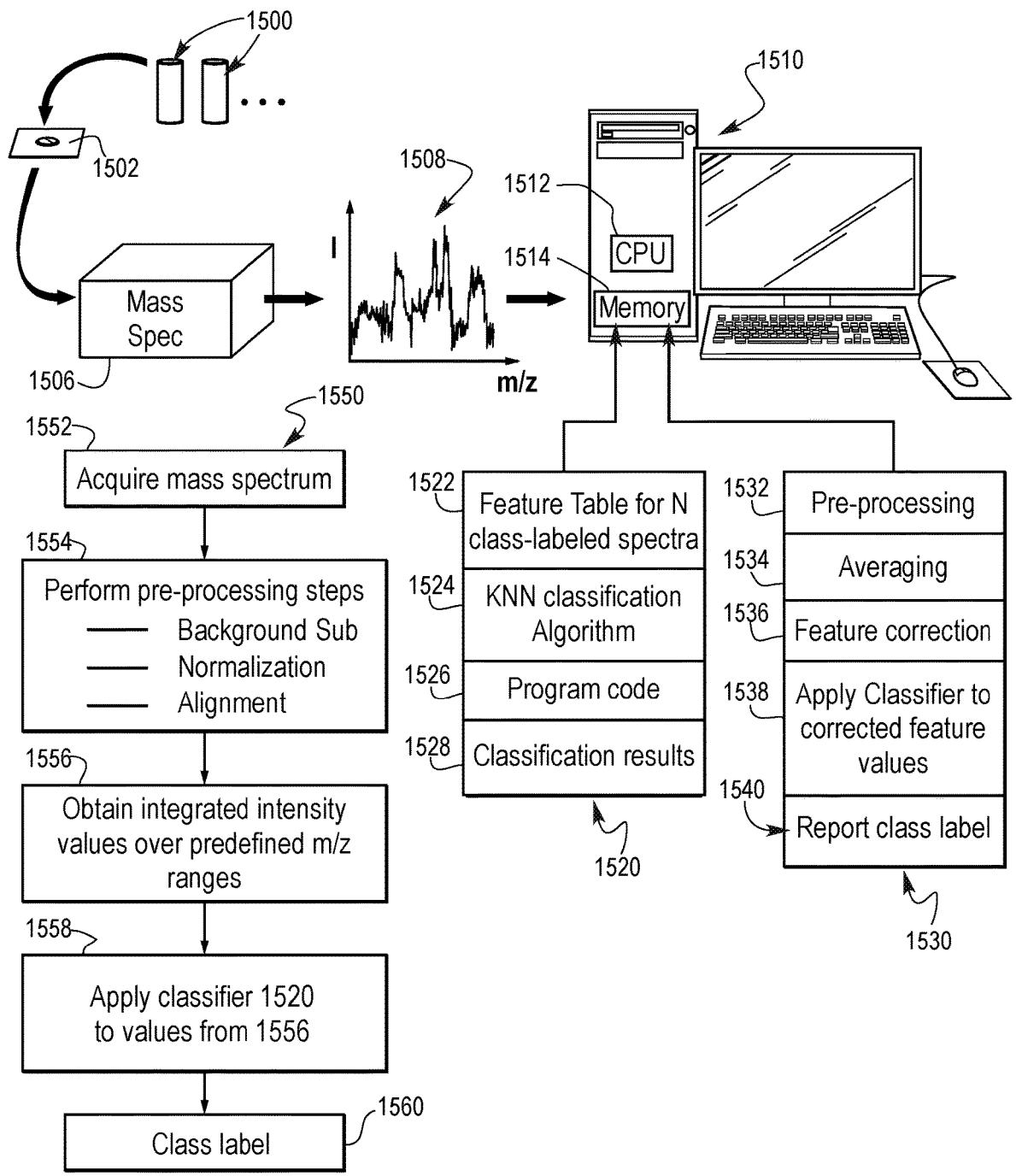
FIG. 15 is a diagram of a practical testing environment for conducting a test on an ovarian cancer patient to make a prediction of the patient's prognosis on platinum-based chemotherapy.

A variation of the construction of the final classifier of FIG. 13 is shown in FIG. 14. The sample is classified initially by Classifier A (1402). At step 1404, a check is made of the classification label. If the label is Early, the sample is classified by Classifier B. At step 1408 a check is made of the class label assigned by Classifier B. If Classifier B also produces a class of Early (branch 1410) the class label of Bad is assigned 1412. If at step 1404 the Classifier A produced the Late class label (1414), or if Classifier B produced the Late class label, the sample is classified by the four third-level classifiers 1418A, 1418B, 1418C and 1418D, in this example corresponding to the C1 . . . C4 classifiers explained above. At step 1420, a check is made to see if each of the four classifiers produced a Late class label. If so, branch 1422 is taken and the Good class label is reported. If at step 1420 the four classifiers do not all produce the Late class label, branch 1426 is taken and the Other class label is reported.

As was the case with the classifier construction of FIG. 12, the "final classifier" shown in FIGS. 13 and 14 is a combination of the individual classifiers A, B and C (or C1 . . . C4 in FIG. 14), plus a set of logical instructions to inspect the class labels produced by the classifiers (including subgroup classifiers) and assign the final class labels as shown in the figures.

Results for Final Classifier Constructed in Accordance with FIG. 14

After the "final classifier" of FIG. 14 was defined and constructed, we subjected the set of samples in the development set to the classification procedure shown in FIG. 14. Twenty eight samples (20%) were classified as Bad, 61 (44%) as Other and 49 (36%) as Good.

The patients' clinical characteristics by classification are shown in table 8.

TABLE 8

Patient characteristics by test classification for classifier run on all the 138 samples

|  |  | Bad (N = 28) n (%) | Other (N = 61) n (%) | Good (N = 49) n (%) | $\chi^2$ p value |
|---|---|---|---|---|---|
| Age | Median | 60 | 60 | 56 | |
|  | (Range) | (41-78) | (18-88) | (18-83) | |
| FIGO | 1 | 0 (0) | 1 (2) | 12 (24) | <0.001 |
|  | 2 | 0 (0) | 2 (3) | 1 (2) | (1 + 2 vs 3 vs 4) |
|  | 3 | 11 (39) | 26 (43) | 17 (35) | |
|  | 4 | 13 (46) | 13 (21) | 3 (6) | |
|  | N/A | 4 (14) | 19 (31) | 16 (33) | |
| Histology Grade | 1 | 0 (0) | 2 (3) | 5 (10) | 0.113 |
|  | 2 | 12 (43) | 20 (33) | 21 (43) | |
|  | 3 | 16 (57) | 39 (64) | 21 (43) | |
| Histology | Non-Serous | 6 (21) | 10 (16) | 22 (45) | 0.003 |
|  | Serous | 22 (79) | 51 (84) | 27 (55) | |
| Residual Tumor | No | 6 (21) | 36 (59) | 43 (88) | <0.001 |
|  | Yes | 22 (79) | 25 (41) | 6 (12) | |
| Metastatic Disease | No | 19 (68) | 52 (85) | 47 (96) | 0.004 |
|  | Yes | 9 (32) | 9 (15) | 2 (4) | |
| "Platinum Resistant" | No | 7 (25) | 39 (64) | 42 (86) | <0.001 |
|  | Yes | 11 (39) | 14 (23) | 6 (12) | (No vs Yes) |
|  | N/A | 10 (36) | 8 (13) | 1 (2) | |

As a test for platinum resistance as assigned by the investigator, classification Bad compared with Other or Good has 35% sensitivity and 92% specificity.

Classification is strongly associated with the known prognostic factors of FIGO score, histology, presence of metastatic disease and presence of residual tumor post-surgery.

Figure 16A:
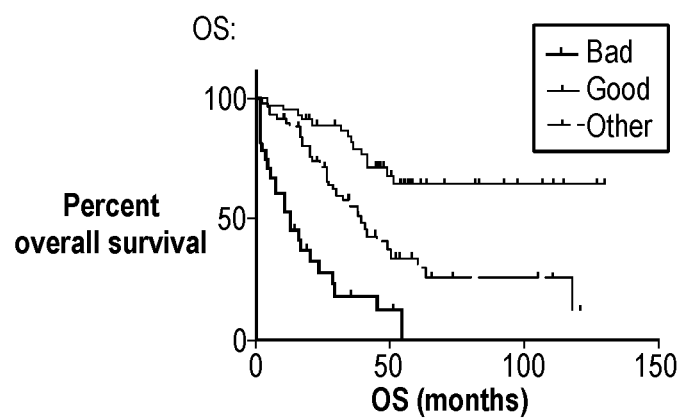
FIGS. 16A and 16B are Kaplan-Meier plots of OS and DFS, respectively by classification group produced on the development sample set using the final classifier construction of FIG. 14.
Figure 16B:
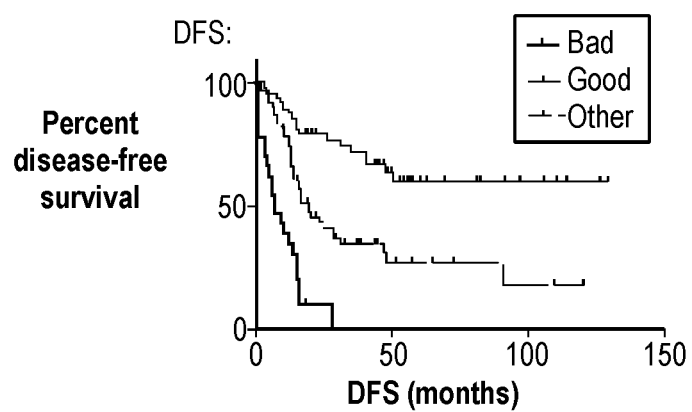

FIGS. 16A and 16B shows the Kaplan-Meier plots by classification group for OS and DFS for the classifications produced by the classifier of FIG. 14. The associated survival analysis statistics are given in tables 9 and 10. Note the extremely poor outcomes, particularly DFS, for the group assigned the label Bad, and the particularly good outcomes for the group assigned the label Good.

TABLE 9

Medians for time-to-event endpoints by classification group

|  | Median OS (95% CI) in months | Median DFS (95% CI) in months |
|---|---|---|
| Bad | 12 (5-23) | 7 (3-14) |
| Other | 39 (28-53) | 20 (14-29) |
| Good | Not reached (51- undefined) | Not reached (48-undefined) |

TABLE 10

Survival analysis statistics between classification groups

|  | OS | | | DFS | | |
|---|---|---|---|---|---|---|
|  | log-rank p | CPH p | HR (95% CI) | log-rank p | CPH p | HR (95% CI) |
| Bad vs Good | <0.001 | <0.001 | 0.13 (0.06-0.26) | <0.001 | <0.001 | 0.10 (0.05-0.22) |
| Bad vs Other | <0.001 | <0.001 | 0.31 (0.18-0.53) | <0.001 | <0.001 | 0.28 (0.16-0.49) |
| Other vs Good | <0.001 | <0.001 | 0.34 (0.18-0.64) | <0.001 | <0.001 | 0.35 (0.19-0.62) |

These results indicate that our hierarchical classifier shown in FIG. 14 is able to stratify the patients into three groups with better, worse, and intermediate outcomes. As can be seen from the data in tables 11 and 12, patients with samples classified as Good are likely to have good long term outcomes on platinum-based chemotherapy, while patients with samples classified as Bad are very unlikely to have good long term outcomes on platinum-based chemotherapy.

TABLE 11

Proportions still alive and disease-free at key timepoints

|  | Bad | Other | Good |
|---|---|---|---|
| % alive at 1 year | 46 | 88 | 96 |
| % alive at 2 years | 28 | 72 | 89 |
| % disease-free at 6 months | 54 | 90 | 96 |
| % disease-free at 1 year | 35 | 75 | 88 |

TABLE 12

Number of patients disease-free at key timepoints

|  | Bad | Other | Good |
|---|---|---|---|
| # DFS ≤ 4 months (N = 14) | 9 (64%) | 3 (21%) | 2 (14%) |
| # DFS > 4 months (N = 121) | 17 (14%) | 57 (47%) | 47 (39%) |
| # DFS ≤ 6 months (N = 20) | 12 (60%) | 6 (30%) | 2 (10%) |
| # DFS > 6 months (N = 115) | 14 (12%) | 54 (47%) | 47 (41%) |
| # DFS ≤ 10 months (N = 32) | 16 (50%) | 11 (34%) | 5 (16%) |
| # DFS >10 months (N = 100) | 9 (9%) | 48 (48%) | 43 (43%) |
| # DFS ≤ 1 year (N = 38) | 17 (45%) | 15 (39%) | 6 (16%) |
| # DFS > 1 year (N = 92) | 8 (9%) | 42 (46%) | 42 (46%) |

In terms of predicting 6 months disease free survival status, a classification of Bad compared with Other or Good has a sensitivity of 60% and specificity of 88%, (odds ratio=0.09 Wald 95% CI: 0.03-0.27). For prediction of 12 months disease free survival status, a classification of Bad compared with Other or Good has a sensitivity of 45% and specificity of 91%.

Table 13 shows the multivariate analysis of classification Bad vs Not Bad (i.e., Other or Good). This shows that while the classification is strongly correlated with other prognostic factors (see table 8), it remains a clearly statistically significant predictor of both OS and DFS when adjusted for other known prognostic factors. This indicates that the classification can provide additional information to other prognostic factors available to physicians.

TABLE 13

Multivariate analysis of OS and DFS

| | OS | | DFS | |
|---|---|---|---|---|
| Covariate | HR (95% Cl) | P value | HR (95% Cl) | P value |
| NotBad (Other or Good) vs Bad | 0.35 (0.20-0.62) | <0.001 | 0.30 (0.17-0.55) | <0.001 |
| FIGO 1-3 vs 4 | 0.35 (0.19-0.63) | <0.001 | 0.52 (0.29-0.93) | 0.027 |
| FIGO NA vs 4 | 0.47 (0.24-0.88) | 0.019 | 0.80 (0.41-1.55) | 0.509 |
| Non-Serous vs Serous | 0.85 (0.46-1.58) | 0.615 | 0.77 (0.43-1.39) | 0.386 |
| Tumor Residual (yes vs no) | 2.25 (1.30-3.90) | 0.004 | 1.81 (1.06-3.08) | 0.031 |

In terms of predicting disease free survival status at six months, the analysis can be adjusted for possible confounding factors using logistic regression. The results are shown in table 14.

TABLE 14

Adjustment of odds ratio for prediction of DFS at 6 months for potential confounding factors

| Covariate | Odds Ratio (95% Cl) | P value |
|---|---|---|
| (Other or Good) vs Bad | 0.18 (0.05-0.65) | 0.009 |
| FIGO 1-3 vs 4 | 0.31 (0.08-1.20) | 0.089 |

TABLE 14-continued

Adjustment of odds ratio for prediction of DFS at 6 months for potential confounding factors

| Covariate | Odds Ratio (95% Cl) | P value |
|---|---|---|
| FIGO NA vs 4 | 0.26 (0.05-1.40) | 0.118 |
| Serous vs Non-Serous | 4.36 (1.17-16.17) | 0.028 |
| Tumor Residual (yes vs no) | 3.05 (0.83-11.25) | 0.094 |

Classification (Bad vs Other or Good) remains a significant predictor of DFS status at 6 months even when adjusted for potential confounding factors.

Conclusions from the Ovarian Cancer/Platinum Chemotherapy Classifiers

We were able to construct classifiers that could separate ovarian cancer patients treated with surgery and platinum based chemotherapy into groups with better and worse outcomes from mass spectra of pretreatment serum samples. The classifier constructed using half of the reduced set of 129 sample set for development (Classifier A) validated well on the remainder of the samples held for internal validation, and the results for the cohort as a whole indicated promising performance. While the test classification was associated with baseline clinical factors known to have prognostic significance, it still showed a trend to statistical significance for providing additional information for prediction of outcomes.

By selecting clinically distinct patient subgroups from the whole cohort to use for classifier development it was possible to construct a classification system composed of multiple hierarchical classifiers that could stratify the ovarian cancer patients into three classes: one with very good outcomes ("Good"), one with very poor outcomes ("Bad") and a third with intermediate outcomes ("Other"). This classification was also strongly correlated with other prognostic factors, but Bad versus Other or Good classifications retained its ability to predict outcome with clear statistical significance even when adjusted for other prognostic factors in multivariate analysis. This indicates that the classification could be of direct clinical utility for physicians advising or making treatment decisions for patients in this indication, providing information supplementary to that available to them from their patients' clinical characteristics.

Interpreted in terms of a test to identify patients who are platinum resistant or platinum refractory, a classification of Bad vs Other or Good showed 60% sensitivity and 88% specificity for identification of patients progressing within 6 months of surgery (odds ratio 0.09). It remained a strong statistically significant predictor of DFS status at six months when adjusted for potential confounding factors, indicating that it again provides physicians with additional information to inform patient care.

The clear potential clinical utility of this test in the adjuvant treatment of ovarian cancer should be validated in an independent cohort of patients (FIG. 5B, step 354).

Laboratory Testing of Samples

Once the classifier (or hierarchical arrangement of classifiers as shown in FIGS. 12, 13 and 14) as described above has been developed, it can now be stored and implemented in a general purpose computer and used to generate a class label for a blood based sample, e.g., in accordance with the predictive test. For example, the class label can predict in advance whether an ovarian cancer patient is likely to have better or worse overall survival on platinum chemotherapy.

FIG. 15 is an illustration of a laboratory testing center or system for processing a test sample (in this example, a blood-based sample from an ovarian cancer patient) using a classifier generated in accordance with the previous discussion. The system includes a mass spectrometer 1506 and a general purpose computer 1510 having CPU 1512 implementing a classifier 1520 coded as machine-readable instructions and a memory 1514 storing a reference mass spectral data set including a feature table 1522 of class-labeled mass spectrometry data. This reference mass spectral data set forming the feature table 1522 will be understood to be the mass spectral data (integrated intensity values of predefined features, see Table 18), associated with a development sample set to create the classifier of FIG. 12, 13 or 14. This data set could be from all the samples, or a subset of the samples (e.g., a development set formed from one half the samples). It will be appreciated that the mass spectrometer 1506 and computer 1510 of FIG. 15 could be used to generate the classifier 1520 in accordance with the process of FIGS. 5A and 5B.

The operation of the system of FIG. 15 will be described in the context of conducting a predictive test for predicting likelihood of a good or a poor outcome of an ovarian cancer patient from platinum chemotherapy. The following discussion assumes that the classifier 1520 is already generated at the time of use of the classifier to generate a class label (Early or Late, Bad, Good, or the equivalent, depending on the exact configuration of the final classifier that is chosen) for a test sample.

The system of FIG. 15 obtains a multitude of samples 1500, e.g., blood-based samples (serum or plasma) from diverse cancer (e.g., ovarian cancer) patients and generates a class label for the sample as a fee-for-service. The samples 1500 are used by the classifier 1520 (implemented in the computer 1510) to make predictions as to whether the patient providing the sample is likely or not likely to have a good outcome on platinum chemotherapy. The outcome of the test is a class label (which may be binary or ternary) such as Early or Late, Good or Bad, Bad or Not Bad, or the like which is assigned to the patient blood-based sample. The particular moniker for the class label is not particularly important and could be generic such as "class 1", "class 2" or the like, but as noted earlier the class label is associated with some clinical attribute relevant to the question being answered by the classifier. While we have disclose binary (Early and Late) and ternary classifiers (Good, Bad, Other) it would in theory be possible to extend to more classes with more subgroup classifiers in classifier C, or more splits of existing classification groups, for example splitting further both the Early and Late groups each into two further groups.

The samples may be obtained on serum cards or the like in which the blood-based sample is blotted onto a cellulose or other type card. Aliquots of the sample are spotted onto one or several spots of a MALDI-ToF sample "plate" 1502 and the plate inserted into a MALDI-ToF mass spectrometer 1506. The mass spectrometer 1506 acquires mass spectra 1508 from each of the spots of the sample. The mass spectra are represented in digital form and supplied to a programmed general purpose computer 1510. The computer 1510 includes a central processing unit 1512 executing programmed instructions. The memory 1514 stores the data representing the mass spectra 1508. Ideally, the sample preparation, spotting and mass spectrometry steps are the same as those used to generate the classifier in accordance with FIGS. 5A and 5B.

The memory 1514 also stores a data set representing a classifier 1520, which includes a) a reference mass spectral data set 1522 in the form of a feature table of N class-labeled spectra, where N is some integer number, in this example a development sample set of spectra used to develop the classifier as explained above or some sub-set of the development sample set. The classifier 1520 includes b) code 1524 representing a KNN classification algorithm (which is implemented in the mini-classifiers as explained above), including the features and depth of the NNN algorithm (parameter s) and identification of all the mini-classifiers passing filtering, c) program code 1526 for executing the final classifier generated in accordance with FIGS. 5A and 5B on the mass spectra of patients, including logistic regression weights and data representing master classifier(s) forming the final classifier, including probability cutoff parameter, mini-classifier filtering criteria, etc., and d) a data structure 1528 for storing classification results, including a final class label for the test sample. The code 1524 also includes the logic for implementing a hierarchical classification procedure such as shown in the construction of the classifiers of FIGS. 12, 13 and 14. The memory 1514 also stores program code 1530 for implementing the processing shown at 1550, including code (not shown) for acquiring the mass spectral data from the mass spectrometer in step 1552; a pre-processing routine 1532 for implementing the background subtraction, normalization and alignment step 1554 (details explained above), filtering and averaging of the 800 shot spectra at multiple locations per spot and over multiple MALDI spots to make a single 100,000+shot average spectrum (as explained above) a module (not shown) for calculating integrated intensity values at predefined m/z positions in the background subtracted, normalized and aligned spectrum (step 1556), and a code routine 1538 for implementing the final classifier 1520 using the reference dataset feature table 1522 on the values obtained at step 1556. The process 1558 produces a class label at step 1560. The module 1540 reports the class label as indicated at 1560 (i.e., "Early" or "Late", "Bad", "Good", "Other" etc. or the equivalent).

The program code 1530 can include additional and optional modules, for example a feature correction function code 1536 (described in co-pending U.S. patent application Ser. No. 14/486,442) for correcting fluctuations in performance of the mass spectrometer, a set of routines for processing the spectrum from a reference sample to define a feature correction function, a module storing feature dependent noise characteristics and generating noisy feature value realizations and classifying such noisy feature value realizations, modules storing statistical algorithms for obtaining statistical data on the performance of the classifier on the noisy feature value realizations, or modules to combine class labels defined from multiple individual replicate testing of a sample to produce a single class label for that sample. Still other optional software modules could be included as will be apparent to persons skilled in the art.

The system of FIG. 15 can be implemented as a laboratory test processing center obtaining a multitude of patient samples from oncologists, patients, clinics, etc., and generating a class label for the patient samples as a fee-for-service. The mass spectrometer 1506 need not be physically located at the laboratory test center but rather the computer 1510 could obtain the data representing the mass spectra of the test sample over a computer network.

Further Considerations

The meaning and use of the "Other" and "Bad" class labels in FIGS. 12, 13, 14 and As noted above, the Other class label is associated with an intermediate outcome on platinum chemotherapy, as compared to the Good and Bad labels. It may well be useful for an ovarian cancer patient to have a more refined idea of her prognosis and to this extent the three classes could have some use. Perhaps in the Other group it might be desirable to consider adding an extra drug to the platinum doublet (e.g., bevacizumab) and this combination is sometimes given. It might also be useful to have the three groups for planning clinical trials. The members of the Bad group clearly have a poor prognosis, and if a therapy helps this class of patients do better it would be great, but if not, these patients will pull down the efficacy of the therapy. The members of the Good group do very well already, so probably the patients cannot do much better. The "Other" group might be the ones to target with new therapies, especially if looking to add on to platinum doublet chemotherapy.

It will be further noted that, if, for clinical use of the test only Bad or Not Bad labels were used, then we would only need Classifiers A and B, and would not need Classifier C at all. In this context, Not Bad means that either Classifier A produced a Late label, or Classifier B produced a Late label. Bad is returned if Classifier A produces an Early class label and Classifier B also produces the Early class label (see FIGS. 13 and 14). Under this scenario, a class label of Bad indicates the patient is likely to be platinum refractory or platinum resistant. Not Bad means that the patient is not likely to be platinum refractory or platinum resistant.

In regards to the Bad class label, the clinical utility of this label is that the patient is likely to be platinum refractory or platinum resistant. The patient being assigned this class label may elect not to proceed with platinum chemotherapy treatment, and consider other options. The surgery for ovarian cancer is very arduous and follow up with a hard chemotherapy, like platinum doublet, makes it harder. Some women may already refuse adjuvant chemotherapy because of this. One use of the Bad label would be that if platinum doublet isn't likely to provide any meaningful benefit, the patient may just opt for no adjuvant therapy and wait until progression/recurrence.

According to the cancer therapy guidelines, there are alternative therapies that are used in higher line, i.e., for recurrence of ovarian cancer. These include: bevacizumab, docetaxel or paclitaxel, etopisode, gemcitabine, doxorubicin, olaparib (PARP inhibitor), topotecan. So, a patient assigned the Bad label could choose no adjuvant therapy and wait to see when recurrence/progression occurs, or potentially they might opt for a therapy approved for higher line treatment, or go on a clinical trial of a new anti-cancer drug.

To summarize, in one aspect we have disclosed a classifier (FIG. 13, 14, 15) predicting in advance whether an ovarian cancer patient is likely to be platinum-refractory or platinum-resistant in treatment of the ovarian cancer with platinum-based chemotherapy, comprising:

a) a machine-readable memory (FIG. 15, 1514) storing a reference set of a class-labeled mass spectral data obtained from blood-based samples of other ovarian cancer patients treated with the platinum-based chemotherapy, the mass spectral data in the form of a feature table (FIG. 2, feature table 50 or reduced feature table) of intensity values of a multitude of mass spectral features, the class label in the form of Early or the equivalent, indicating that the sample was from a patient that did relatively poorly on platinum-based chemotherapy in treatment of the ovarian cancer, or Late or the equivalent, indicating that the sample was from a patient that did relatively well on platinum-based chemotherapy in treatment of the ovarian cancer with platinum-based chemotherapy.

The classifier further includes:

b) a programmed computer (FIG. 15, 1510) implementing a classification algorithm (1520) comparing mass spectral data of a sample to be tested with the reference set and generating a class label for the sample to be tested. The classification algorithm implements a hierarchical multi-level classification including at a first level and a second level (see FIGS. 13, 14, Classifier A and Classifier B, respectively), wherein the classification algorithm at the first level produces a class label of Early or Late or the equivalent, and if the class label at the first level is Early or the equivalent the classification algorithm proceed to a second level (Classifier B) and uses a subset of the reference set in the form of patients identified with the class label Early or the equivalent further stratified into Early (or Earlier) and Late (or Later) class labels (see description of Classifier B). The classification algorithm at the second level identifies patients as likely to be platinum-refractory or platinum-resistant in treatment of the ovarian cancer with platinum-based chemotherapy (class label Bad or the equivalent, FIGS. 13 and 14).

In one embodiment, the reference set includes feature values for the mass spectral features listed in Table 18. In a preferred embodiment the mass spectral data forming the reference set and are obtained in MALDI-TOF mass spectrometry by subjecting the sample to at least 100,000 laser shots.

As shown in FIGS. 13 and 14, the hierarchical multi-level classification may include a third classification level (Classifier C), wherein a class label assigned at the third classification level is used to identify patients as being likely to have particularly good outcomes on the platinum-based chemotherapy (class label Good or the equivalent, see FIGS. 13 and 14).

As explained in the description of the development of Classifier C, this classifier includes multiple classifiers developed from one or more different clinical sub-groups of a classifier development set used to generate the first level classifier. For example the third classification level includes four different classifiers C1, C2, C3, and C4, each developed from the following different clinical sub-groups:

C1: a subset of patients with non-serous histology or serous histology together with unknown FIGO score;

C2: a subset of patients not used to develop Classifier C1 who all have serous histology;

C3: a subset of patients with residual tumor after surgery.

C4: a subset of patients with no residual tumor after surgery.

In another aspect, a multi-stage classifier has been described comprising:

a programmed computer (1510. FIG. 15) implementing a hierarchical classification algorithm (FIG. 13, 14) operating on mass spectral data of a test sample stored in memory and making use of a reference set of class-labeled mass spectral data stored in the memory;

wherein the classification algorithm further comprises:

a first stage classifier for stratifying the test mass spectral data into either an Early or Late group (Classifier A, FIG. 13);

a second stage classifier (Classifier B) for further stratifying the Early group of the first stage classifier into Early and Late groups (or Earlier and Later groups, or the equivalent), the second stage implemented if the first stage classifier classifies the test mass spectral data into the Early group and the Early or the equivalent class label produced by the second stage classifier is associated with an exceptionally poor prognosis, overall class label Bad or the equivalent (See discussion of FIGS. 13 and 14); and a third stage classifier (Classifier C) for further stratifying the Late group of the first stage classifier into Early and Late groups (or Earlier and Later groups, or the equivalent), the third stage classifier implemented if the first stage classifier classifies the test mass spectral data into the Late group, wherein a Late class label (or the equivalent) produced by the third stage classifier is associated with an exceptionally good prognosis, e.g., overall class label Good or the equivalent, as shown in FIGS. 13 and 14.

As shown in FIG. 14, the third stage classifier can take the form of one or more classifiers developed from one or more different clinical sub-groups of a classifier development set used to generate the first level classifier, such as for example four different classifiers C1, C2, C3, and C4, each developed from different clinical sub-groups.

In another aspect, a method of generating a classifier for classifying a test sample from a development set of samples, each of the samples being associated with clinical data, has been described comprising the steps of:

(a) dividing the development set of samples into different clinical subgroups 1 . . . N based on the clinical data, where N is an integer of at least 2 (see FIG. 11);

(b) performing a classifier development process (such as for example the process of FIG. 5) for each of the different clinical subgroups 1 . . . N, thereby generating N different classifiers C1 . . . CN (FIG. 11); and (c) defining a final classification process whereby a patient sample is classified by the classifiers C1 . . . CN (FIG. 12, 13 or 14).

In still another aspect, a method of generating a classifier for classifying a test sample has been described comprising the steps of:

(a) generating a classifier from measurement data of a development set of samples using a classifier development process (development of Classifier A, e.g. using the procedure of FIGS. 5A and 5B);

(b) dividing the development set of samples into different clinical subgroups 1 . . . N where N is an integer of at least 2 (see FIG. 11);

(c) repeating the classifier development process (FIGS. 5A and 5B) for each of the different clinical subgroups 1 . . . N, thereby generating different classifiers C1 . . . CN (FIG. 11); and (d) defining a hierarchical classification process whereby a patient sample is classified first by the classifier generated in step a) and then by the classifiers C1 . . . CN. See FIGS. 13, 14.

In still another aspect, we have also described a method of generating a classifier for classifying a test sample, comprising the steps of:

(a) generating a first classifier from measurement data of a development set of samples using a classifier development process (Classifier A);

(b) performing a classification of the measurement data of the development set of samples using the first classifier, thereby assigning each member of the development set of samples with a class label in a binary classification scheme (Early/Late, or the equivalent);

(c) generating a second classifier (Classifier B) using the classifier development process with an input classifier development set being the members of the development set assigned one of the two class labels in the binary classification scheme by the first classifier (in the present example the Early samples; optionally this development set may be augmented by other poorly performing samples which were excluded from development of classifier A), the second classifier thereby stratifying the members of the set with the first class label into two further sub-groups. See description of development of Classifier B.

This method may further include additional steps of (d) dividing the development set of samples into different clinical subgroups 1 . . . N where N is an integer of at least 2 (FIG. 11);

(e) repeating the classifier development process for each of the different clinical subgroups 1 . . . N, thereby generating N different third classifiers C1 . . . CN (FIG. 11) and (f) defining a hierarchical classification process (FIG. 14) whereby:

i. a patient sample is classified first by the first classifier (Classifier A) generated in step a);

ii. if the class label assigned by the first classifier is the class label used to generate the second classifiers (Early in this example), then classifying the patient sample with the second classifier (Classifier B): and iii. if the class label assigned by the first classifier is not the class label used to generate the second classifier (i.e., Late or the equivalent), then classifying the patient sample with the third classifiers C1 . . . CN (see FIG. 14); and iv. generating a final label as a result of classification steps ii or step iii (Good or Bad or the equivalent).

In still another aspect, a classifier generation method has been described including the steps of:

a) obtaining physical measurement data from a development set of samples (e.g., mass spectrometry, see FIG. 2) and supplying the measurement data to a general purpose computer FIG. 2, 42), each of the samples further associated with clinical data;

b) generating a first classifier (Classifier A) from the measurement data of the development set of samples;

c) identifying a plurality of different clinical sub-groups C1 . . . CN within the development set based on the clinical data (FIG. 11);

d) for each of the different clinical sub-groups, conducting a classifier generation process (FIGS. 5A and 5B) from the measurement data for each of the members of the development set that is associated with such clinical sub-groups thereby generating clinical subgroup classifiers C1 . . . CN (FIG. 11); and e) storing in memory of a computer a classification procedure involving Classifier A and the classifiers C1 . . . CN developed in step c), (FIG. 12, 13 or 14).

As shown by way of example above, the classifier development is optionally in accordance with the CMC/D classifier development process of FIGS. 5A and 5B.

In one embodiment the method may further include a step of conducting a bagged filtering operation (FIGS. 2A, 3 and 4) to filter the measurement data obtained from the samples to either deselect junky features in the measurement data or select a subset of the features in the measurement data which have significant classification performance; and wherein the deselection of junky features or selection of a subset of features which have significant classification performance is repeated at for each refinement of class labels undertaken during the process shown in FIG. 5. For example the initial mass spectrometry of the samples in the development set may yield 300 or 350 potential peaks for use in classifier generation but this list can be filtered in a selection manner to yield say just 50 or 60 features. See Table 18 for a listing of the features which are used in the classifiers of this disclosure.

In one embodiment, the measurement data comprises MALDI-TOF mass spectrometry data. In principle, the methods of classifier development could use other forms of data such as protein expression, mRNA transcript expression level or other type of proteomic or genomic data.

If MALDI-TOF mass spectrometry data is used, preferably it is acquired from a process in which each of the samples in the development set is subject to at least 100.000 laser shots, such as described in detail above or in the Deep MALDI patent cited previously.

Further variations from the particulars of the illustrated embodiment are contemplated. The appended claims are offered by way of description of the disclosed inventions.

TABLE 15

| Sample split into development set and validation set for the 129 sample classifier 129 sample classifier | |
|---|---|
| Sample ID | Set |
| 185687 | Validation |
| 186107 | Development |
| 186405 | Development |
| 186758 | Development |
| 186811 | Development |
| 186955 | Development |
| 187073 | Validation |
| 187692 | Validation |
| 187800 | Development |
| 188006 | Validation |
| 188572 | Validation |
| 188627 | Validation |
| 188661 | Validation |
| 188733 | Development |
| 188840 | Development |
| 188856 | Development |
| 189850 | Development |
| 189943 | Development |
| 190001 | Development |
| 190011 | Validation |
| 190060 | Development |
| 190065 | Development |
| 190089 | Validation |
| 190107 | Validation |
| 190140 | Development |
| 190178 | Development |
| 190234 | Development |
| 190265 | Development |
| 190507 | Development |
| 190677 | Development |
| 190780 | Development |
| 190861 | Validation |
| 190937 | Development |
| 190943 | Development |
| 190954 | Development |
| 190985 | Validation |
| 191125 | Validation |
| 191147 | Validation |
| 191154 | Validation |
| 191210 | Validation |
| 191227 | Development |
| 191305 | Development |
| 191336 | Validation |
| 191407 | Validation |
| 191454 | Development |
| 191484 | Development |
| 191526 | Validation |
| 191650 | Validation |
| 191709 | Validation |
| 191812 | Validation |
| 191899 | Development |
| 191926 | Development |
| 191966 | Development |
| 191972 | Development |
| 191976 | Development |
| 191982 | Development |
| 191997 | Development |
| 192109 | Development |

TABLE 15-continued

| Sample split into development set and validation set for the 129 sample classifier 129 sample classifier | |
|---|---|
| Sample ID | Set |
| 192150 | Validation |
| 192158 | Development |
| 192196 | Validation |
| 192249 | Validation |
| 192271 | Validation |
| 192341 | Validation |
| 192542 | Validation |
| 192645 | Development |
| 192663 | Validation |
| 192682 | Validation |
| 192693 | Development |
| 192789 | Development |
| 192833 | Development |
| 192852 | Development |
| 192865 | Validation |
| 193094 | Development |
| 193105 | Development |
| 193146 | Validation |
| 193214 | Validation |
| 193371 | Development |
| 193396 | Validation |
| 193579 | Validation |
| 193975 | Development |
| 194036 | Development |
| 194126 | Validation |
| 194349 | Validation |
| 194460 | Development |
| 194794 | Validation |
| 194891 | Validation |
| 194910 | Development |
| 195309 | Validation |
| 195426 | Validation |
| 195555 | Development |
| 195564 | Validation |
| 195581 | Validation |
| 195649 | Development |
| 196132 | Validation |
| 196166 | Development |
| 196446 | Validation |
| 196489 | Validation |
| 196625 | Development |
| 196678 | Validation |
| 196681 | Development |
| 196718 | Development |
| 196770 | Validation |
| 196963 | Development |
| 197110 | Development |
| 197152 | Development |
| 197202 | Validation |
| 197619 | Validation |
| 197626 | Development |
| 197704 | Validation |
| 197793 | Validation |
| 197800 | Development |
| 197838 | Development |
| 847746 | Validation |
| 848072 | Development |
| 848172 | Validation |
| 848389 | Validation |
| 848578 | Validation |
| 848740 | Validation |
| 848820 | Validation |
| 848847 | Validation |
| 848998 | Development |
| 849167 | Development |
| 849671 | Validation |
| 849706 | Development |
| 849769 | Validation |
| 853522 | Validation |
| 853631 | Validation |
| 854327 | Validation |

TABLE 16

Summary of Sample Classifications (Classifier A)

| Sample ID | Classification |
|---|---|
| 185687 | Late |
| 185961 | Early |
| 186107 | Early |
| 186405 | Late |
| 186758 | Late |
| 186811 | Late |
| 186955 | Early |
| 187073 | Late |
| 187692 | Late |
| 187800 | Late |
| 187904 | Early |
| 188006 | Late |
| 188572 | Early |
| 188627 | Early |
| 188661 | Late |
| 188733 | Late |
| 188840 | Late |
| 188856 | Late |
| 189850 | Late |
| 189943 | Late |
| 190001 | Early |
| 190011 | Late |
| 190060 | Late |
| 190065 | Early |
| 190089 | Early |
| 190107 | Early |
| 190140 | Early |
| 190178 | Early |
| 190234 | Late |
| 190265 | Late |
| 190507 | Late |
| 190677 | Early |
| 190780 | Early |
| 190861 | Early |
| 190937 | Early |
| 190943 | Early |
| 190954 | Early |
| 190985 | Early |
| 191125 | Late |
| 191147 | Late |
| 191154 | Late |
| 191210 | Early |
| 191227 | Early |
| 191305 | Late |
| 191336 | Late |
| 191407 | Late |
| 191454 | Late |
| 191484 | Early |
| 191526 | Late |
| 191650 | Late |
| 191661 | Early |
| 191709 | Late |
| 191812 | Early |
| 191899 | Late |
| 191926 | Late |
| 191966 | Late |
| 191972 | Early |
| 191976 | Late |
| 191982 | Early |
| 191997 | Late |
| 192109 | Late |
| 192150 | Late |
| 192158 | Late |
| 192196 | Late |
| 192249 | Early |
| 192271 | Late |
| 192341 | Late |
| 192487 | Late |
| 192542 | Late |
| 192645 | Late |
| 192663 | Late |
| 192682 | Late |
| 192693 | Late |
| 192789 | Late |
| 192833 | Late |
| 192852 | Late |
| 192865 | Early |
| 193094 | Early |
| 193105 | Late |
| 193146 | Late |
| 193214 | Late |
| 193371 | Late |
| 193396 | Late |
| 193579 | Early |
| 193975 | Early |
| 194036 | Early |
| 194126 | Early |
| 194335 | Late |
| 194349 | Early |
| 194460 | Late |
| 194791 | Late |
| 194794 | Late |
| 194891 | Early |
| 194910 | Late |
| 195309 | Early |
| 195426 | Late |
| 195555 | Early |
| 195564 | Late |
| 195581 | Early |
| 195649 | Late |
| 195992 | Early |
| 196132 | Late |
| 196166 | Late |
| 196446 | Early |
| 196489 | Late |
| 196625 | Late |
| 196678 | Late |
| 196681 | Early |
| 196718 | Late |
| 196770 | Early |
| 196963 | Late |
| 197110 | Late |
| 197152 | Late |
| 197202 | Early |
| 197619 | Late |
| 197626 | Early |
| 197668 | Late |
| 197704 | Late |
| 197793 | Early |
| 197800 | Early |
| 197838 | Late |
| 847746 | Early |
| 848072 | Early |
| 848172 | Early |
| 848389 | Late |
| 848410 | Early |
| 848578 | Late |
| 848740 | Late |
| 848820 | Late |
| 848847 | Early |
| 848998 | Early |
| 849167 | Early |
| 849671 | Late |
| 849706 | Late |
| 849769 | Early |
| 853522 | Late |
| 853631 | Late |
| 854327 | Late |

TABLE 17

Summary of Sample Classifications
(Final Classifier of FIG. 14)

| Sample ID | Final Classification |
|---|---|
| 185687 | Good |
| 185961 | Bad |
| 186107 | Other |

TABLE 17-continued

Summary of Sample Classifications
(Final Classifier of FIG. 14)

| Sample ID | Final Classification |
| --- | --- |
| 186405 | Good |
| 186758 | Other |
| 186811 | Good |
| 186955 | Bad |
| 187073 | Good |
| 187692 | Good |
| 187800 | Good |
| 187904 | Other |
| 188006 | Good |
| 188572 | Bad |
| 188627 | Other |
| 188661 | Good |
| 188733 | Other |
| 188840 | Good |
| 188856 | Other |
| 189850 | Other |
| 189943 | Other |
| 190001 | Other |
| 190011 | Other |
| 190060 | Other |
| 190065 | Other |
| 190089 | Bad |
| 190107 | Bad |
| 190140 | Bad |
| 190178 | Other |
| 190234 | Good |
| 190265 | Good |
| 190507 | Good |
| 190677 | Other |
| 190780 | Other |
| 190861 | Other |
| 190937 | Other |
| 190943 | Bad |
| 190954 | Other |
| 190985 | Bad |
| 191125 | Good |
| 191147 | Other |
| 191154 | Good |
| 191210 | Bad |
| 191227 | Other |
| 191305 | Good |
| 191336 | Good |
| 191407 | Good |
| 191454 | Other |
| 191484 | Other |
| 191526 | Other |
| 191650 | Other |
| 191661 | Bad |
| 191709 | Good |
| 191812 | Bad |
| 191899 | Good |
| 191926 | Good |
| 191966 | Good |
| 191972 | Bad |
| 191976 | Other |
| 191982 | Other |
| 191997 | Good |
| 192109 | Other |
| 192150 | Good |
| 192158 | Good |
| 192196 | Good |
| 192249 | Other |
| 192271 | Other |
| 192341 | Other |
| 192487 | Bad |
| 192542 | Good |
| 192645 | Good |
| 192663 | Good |
| 192682 | Good |
| 192693 | Other |
| 192789 | Other |
| 192833 | Good |
| 192852 | Good |
| 192865 | Bad |
| 193094 | Other |
| 193105 | Good |
| 193146 | Good |
| 193214 | Other |
| 193371 | Good |
| 193396 | Good |
| 193579 | Other |
| 193975 | Other |
| 194036 | Other |
| 194126 | Other |
| 194335 | Bad |
| 194349 | Other |
| 194460 | Good |
| 194791 | Bad |
| 194794 | Good |
| 194891 | Bad |
| 194910 | Other |
| 195309 | Other |
| 195426 | Good |
| 195555 | Other |
| 195564 | Other |
| 195581 | Bad |
| 195649 | Good |
| 195992 | Bad |
| 196132 | Other |
| 196166 | Other |
| 196446 | Other |
| 196489 | Good |
| 196625 | Good |
| 196678 | Good |
| 196681 | Other |
| 196718 | Good |
| 196770 | Bad |
| 196963 | Other |
| 197110 | Good |
| 197152 | Other |
| 197202 | Bad |
| 197619 | Other |
| 197626 | Bad |
| 197668 | Bad |
| 197704 | Other |
| 197793 | Other |
| 197800 | Bad |
| 197838 | Good |
| 847746 | Other |
| 848072 | Other |
| 848172 | Other |
| 848389 | Good |
| 848410 | Bad |
| 848578 | Other |
| 848740 | Other |
| 848820 | Good |
| 848847 | Bad |
| 848998 | Other |
| 849167 | Bad |
| 849671 | Other |
| 849706 | Good |
| 849769 | Bad |
| 853522 | Other |
| 853631 | Other |
| 854327 | Good |

TABLE 18

Features Used in Each Classifier
Fifty six features were used in classifier A, 66 in classifier B, 59 in classifier $C_1$, 67 in classifier $C_2$, 57 in classifier $C_3$, and 56 in classifier $C_4$.

| Classifier A | Classifier B | Classifier $C_1$ | Classifier $C_2$ | Classifier $C_3$ | Classifier $C_4$ |
|---|---|---|---|---|---|
| 3243 | 3110 | 3465 | 3465 | 3420 | 3445 |
| 3364 | 3776 | 3679 | 3679 | 3755 | 3465 |
| 3755 | 3842 | 4340 | 3703 | 4210 | 3818 |
| 3887 | 4133 | 4381 | 3755 | 4340 | 4099 |
| 3928 | 4459 | 4590 | 3818 | 4381 | 4590 |
| 4286 | 4773 | 4856 | 3928 | 5041 | 4856 |
| 4340 | 4791 | 5068 | 4340 | 5129 | 5158 |
| 4381 | 4999 | 5104 | 4381 | 5359 | 5180 |
| 4507 | 5041 | 5674 | 4590 | 5403 | 5198 |
| 4590 | 5145 | 5706 | 4718 | 5706 | 5430 |
| 4918 | 5198 | 5720 | 4818 | 5720 | 5674 |
| 5041 | 5224 | 5777 | 4938 | 5777 | 5706 |
| 5068 | 5359 | 6485 | 5041 | 5795 | 6091 |
| 5104 | 5430 | 6534 | 5129 | 6315 | 6109 |
| 5129 | 5674 | 6568 | 5416 | 6438 | 6589 |
| 5521 | 6109 | 6589 | 5720 | 6485 | 6789 |
| 5691 | 6122 | 6657 | 5748 | 6612 | 6881 |
| 5720 | 6210 | 6789 | 5762 | 6881 | 6898 |
| 5734 | 6268 | 6881 | 5816 | 6898 | 7274 |
| 5748 | 6301 | 6898 | 5842 | 6922 | 7301 |
| 5795 | 6589 | 6922 | 5867 | 7334 | 7420 |
| 6153 | 6612 | 6992 | 5911 | 7474 | 8207 |
| 6170 | 6634 | 7022 | 6153 | 7779 | 8430 |
| 6568 | 6657 | 7035 | 6315 | 8315 | 8974 |
| 6881 | 6761 | 7274 | 6860 | 8565 | 9098 |
| 6898 | 6789 | 7739 | 6881 | 8585 | 9109 |
| 6922 | 7022 | 7779 | 7318 | 8771 | 9208 |
| 6992 | 7074 | 8254 | 8315 | 8974 | 9395 |
| 7779 | 7441 | 8565 | 8531 | 9245 | 9484 |
| 8184 | 7779 | 8585 | 8771 | 9359 | 9504 |
| 8585 | 7913 | 8771 | 9038 | 9395 | 9535 |
| 8771 | 8254 | 9395 | 9187 | 10012 | 9721 |
| 9187 | 8315 | 9504 | 9208 | 10589 | 9793 |
| 9395 | 8391 | 9535 | 9264 | 11067 | 10079 |
| 10135 | 8974 | 9721 | 9359 | 11149 | 10236 |
| 10304 | 9208 | 9793 | 9395 | 11481 | 10263 |
| 11045 | 9245 | 9941 | 9430 | 11527 | 10419 |
| 11067 | 9319 | 10263 | 9535 | 11576 | 11197 |
| 11149 | 9576 | 11067 | 9641 | 11632 | 12674 |
| 11376 | 10263 | 12873 | 10012 | 11787 | 13275 |
| 12321 | 10285 | 13275 | 10185 | 11899 | 13365 |
| 13134 | 10419 | 13323 | 10210 | 12003 | 13568 |
| 13323 | 10802 | 13525 | 10236 | 12233 | 13615 |
| 13615 | 11104 | 13568 | 10304 | 12291 | 13721 |
| 13762 | 12233 | 13615 | 10847 | 12321 | 13762 |
| 13798 | 13275 | 13798 | 11045 | 13762 | 13984 |
| 13843 | 14098 | 13843 | 11067 | 13843 | 14043 |
| 13984 | 14149 | 13984 | 11376 | 14043 | 14149 |
| 17395 | 14199 | 14098 | 11481 | 14098 | 14199 |
| 17476 | 14255 | 14149 | 11733 | 14149 | 15629 |
| 17604 | 14307 | 14199 | 11835 | 15751 | 18275 |
| 18637 | 14595 | 14255 | 12321 | 21688 | 18850 |
| 18729 | 15563 | 17604 | 12873 | 23036 | 21062 |
| 18850 | 15629 | 18637 | 12968 | 23146 | 23036 |
| 23036 | 16630 | 18729 | 13081 | 23249 | 27944 |
| 23146 | 17033 | 18850 | 13365 | 23357 | 28082 |
|  | 17148 | 20946 | 13568 | 23469 |  |
|  | 17271 | 21062 | 13615 |  |  |
|  | 17476 | 27944 | 13762 |  |  |
|  | 18275 |  | 13798 |  |  |
|  | 20946 |  | 13843 |  |  |
|  | 21062 |  | 14043 |  |  |
|  | 21170 |  | 15563 |  |  |
|  | 21275 |  | 15751 |  |  |
|  | 21377 |  | 18729 |  |  |
|  | 21816 |  | 19992 |  |  |
|  |  |  | 28082 |  |  |

We claim:

1. A classifier predicting in advance whether an ovarian cancer patient is likely to be platinum-refractory or platinum-resistant in treatment of the ovarian cancer with platinum-based chemotherapy, the classifier comprising:
   a) a machine-readable memory storing a reference set of class-labeled mass spectral data obtained from blood-based samples of other ovarian cancer patients treated with the platinum-based chemotherapy, the mass spectral data included in a feature table of intensity values of a multitude of mass spectral features, the samples classified with class labels including an Early class label, indicating that the sample was from a patient that performed relatively poorly on platinum-based chemotherapy, or including a Late class label, indicating the that the sample was from a patient that performed relatively well on platinum-based chemotherapy in treatment of the ovarian cancer;
   b) a programed computer implementing a classification algorithm comparing mass spectral data of a sample to be tested with the reference set and generating a class label for the sample to be tested;
      wherein the mass spectral data of the sample to be tested is obtained from a mass spectrometer configured to generate the mass spectral data of the sample to be tested,
   wherein the classification algorithm implements a hierarchical multi-level classification in series including at least a first level and a second level, the hierarchical multi-level classification is generated by:
      generating a plurality of mini-classifiers that include identified sets of feature values in the mass spectral features, wherein the plurality of mini-classifiers are generated using a k-nearest neighbor (kNN) classification algorithm;
      deriving, for each of the plurality of mini-classifiers, a set of proposed classifications for each of the samples in the reference set;
      identifying a subset of mini-classifiers with a threshold number of proposed classifications that correspond with class labels for the samples in the reference set; and
      combining each of the subset of mini-classifiers to generate a master classifier, wherein the hierarchical multi-level classification is generated at least from the master classifier;
   wherein the classification algorithm at the first level produces a class label for the sample to be tested including either the Early class label or Late class label, the Late class label identifies patients as being likely to not be platinum-refractory or platinum-resistant in treatment of the ovarian cancer with platinum-based chemotherapy, and
   responsive to the classification algorithm determining that the class label for the sample to be tested at the first level comprises the Early class label, the classification algorithm proceeds to a second level and uses a subset of the reference set in the form of patients identified with the class label Early further stratified into an Earlier class label and a Later class label, and the classification algorithm at the second level identifies patients as likely to be platinum-refractory or platinum-resistant in treatment of the ovarian cancer with platinum-based chemotherapy; and
   transmitting a report message comprising the class label for the sample to be tested to a client device.

2. The classifier of claim 1, wherein the reference set includes feature values for the mass spectral features listed in Table 18.

3. The classifier of claim 1, wherein the mass spectral data forming the reference set are obtained in MALDI-TOF mass spectrometry by subjecting the sample to at least 100,000 laser shots.

4. The classifier of claim 1, wherein the hierarchical multi-level classification includes a third classification level, wherein a class label assigned at the third classification level is used to identify patients as being likely to have particularly good outcomes on the platinum-based chemotherapy.

5. The classifier of claim 4, wherein the third classification level includes one or more classifiers developed from one or more different clinical sub-groups of a classifier development set used to generate the first level classifier.

6. The classifier of claim 5, wherein the third classification level includes four different classifiers C1, C2, C3, and C4, each developed from the following different clinical sub-groups:
C1: a subset of patients with non-serous histology or serous histology together with unknown FIGO score;
C2: a subset of patients with serous histology not used to develop Classifier C1;
C3: a subset of patients with residual tumor after surgery;
C4: a subset of patients with no residual tumor after surgery.

7. A multi-stage classifier comprising:
a programmed computer implementing a hierarchical classification procedure operating on test mass spectral data of a test sample stored in memory and making use of a reference set of class-labeled mass spectral data stored in the memory, wherein generation of the hierarchical classification procedure comprises:
obtaining the test mass spectral data of the test sample from a mass spectrometer configured to generate the test mass spectral data of the test sample;
receiving the reference set of class-labeled mass spectral data comprising mass spectral data obtained from blood-based samples of other ovarian cancer patients treated with platinum-based chemotherapy, the mass spectral data included in a feature table of intensity values of a multitude of mass spectral features;
generating a plurality of mini-classifiers that include identified sets of feature values in the mass spectral features, wherein the plurality of mini-classifiers are generated using a k-nearest neighbor (kNN) classification algorithm;
deriving, for each of the plurality of mini-classifiers, a set of proposed classifications for each sample in the reference set;
identifying a subset of mini-classifiers with a threshold number of proposed classifications that correspond with class labels for the samples in the reference set; and
combining each of the subset of mini-classifiers to generate a master classifier, wherein the hierarchical classification procedure utilizes at least the master classifier;
wherein the classification procedure further comprises:
a first stage classifier for stratifying the test mass spectral data into either an Early or Late group;
a second stage classifier for further stratifying the Early group of the first stage classifier into Early and Late groups or Earlier and Later groups, the second stage implemented if the first stage classifier classifies the test mass spectral data into the Early group and the Early class label produced by the second stage classifier is associated with an exceptionally poor prognosis;
a third stage classifier for further stratifying the Late group of the first stage classifier into Early and Late groups or Earlier and Later groups, the third stage classifier implemented if the first stage classifier classifies the test mass spectral data into the Late group, wherein a Late class label produced by the third stage classifier is associated with an exceptionally good prognosis.

8. The multi-stage classifier of claim 7, wherein the third stage classifier comprises one or more classifiers developed from one or more different clinical sub-groups of a classifier development set used to generate the first level classifier.

9. The multi-stage classifier of claim 8, wherein the third stage classifier includes four different classifiers C1, C2, C3, and C4, each developed from different clinical sub-groups.

10. The multi-stage classifier of claim 9, wherein the multi-stage classifier is configured to predict an ovarian cancer patient as being likely or not likely to benefit from platinum chemotherapy, and wherein the classifiers C1, C2 C3 and C4 are developed from the following clinical sub-groups:
C1: developed from a subset of patients with non-serous histology or serous histology together with unknown FIGO score;
C2: developed from a subset of patients with serous histology not used to develop Classifier C1;
C3: developed from a subset of patients with residual tumor after surgery;
C4: developed from a subset of patients with no residual tumor after surgery.

11. A method of generating a classifier for classifying a test sample from a development set of samples, each of the samples being associated with clinical data, comprising the steps of:
obtaining a patient sample of mass spectral data from a mass spectrometer configured to generate the patient sample of mass spectral data;
receiving a development set of class-labeled mass spectral data comprising mass spectral data obtained from blood-based samples of other ovarian cancer patients treated with platinum-based chemotherapy, the mass spectral data included in a feature table of intensity values of a multitude of mass spectral features;
(a) dividing the development set of samples into different clinical subgroups 1 . . . N based on the clinical data, where N is an integer of at least 2;
(b) performing a classifier development process for each of the different clinical subgroups 1 . . . N, thereby generating different classifiers C1 . . . CN;
generating, for mass spectral data corresponding to each different clinical subgroup, a plurality of mini-classifiers that include identified sets of feature values in the mass spectral features, wherein the plurality of mini-classifiers are generated using a k-nearest neighbor (kNN) classification algorithm;
deriving, for each of the plurality of mini-classifiers, a set of proposed classifications for each sample in the reference set;
identifying a subset of mini-classifiers with a threshold number of proposed classifications that correspond with class labels for the samples in the reference set; and
combining, for each of the different clinical subgroups, each of the subset of mini-classifiers to generate a master classifier, wherein the master classifiers generated for each of the different clinical subgroups are combined as part of a hierarchical multi-level classifier;

(c) defining a final classification process whereby a patient sample is classified using the hierarchical multi-level classifier by the classifiers C1 ... CN; and transmitting the classifiers corresponding with the patient sample to a client device.

* * * * *